United States Patent
Mercer et al.

(10) Patent No.: US 9,950,122 B2
(45) Date of Patent: Apr. 24, 2018

(54) PEN TYPE DRUG INJECTION DEVICE WITH FRICTION REDUCING DOSE ENCODER MECHANISM

(71) Applicant: Sanofi-Aventis Deutschland GmbH, Frankfurt am Main (DE)

(72) Inventors: David Richard Mercer, Dorset (GB); Paul Richard Draper, Worcestershire (GB); Anthony Paul Morris, West Midlands (GB); Stephen Francis Gilmore, Bristol (GB); George Cave, Warwickshire (GB); Samuel Steel, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 461 days.

(21) Appl. No.: 14/759,902

(22) PCT Filed: Jan. 13, 2014

(86) PCT No.: PCT/EP2014/050461
§ 371 (c)(1),
(2) Date: Jul. 8, 2015

(87) PCT Pub. No.: WO2014/111335
PCT Pub. Date: Jul. 24, 2014

(65) Prior Publication Data
US 2015/0352287 A1     Dec. 10, 2015

(30) Foreign Application Priority Data
Jan. 15, 2013 (EP) .................................... 13151364

(51) Int. Cl.
*A61M 5/00*     (2006.01)
*A61M 5/315*    (2006.01)
(Continued)

(52) U.S. Cl.
CPC .... *A61M 5/31546* (2013.01); *A61M 5/31525* (2013.01); *A61M 5/31535* (2013.01);
(Continued)

(58) Field of Classification Search
CPC .......... A61M 5/31546; A61M 5/31525; A61M 5/31535; A61M 5/31551; A61M 5/31566
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 102202711 A | 9/2011 |
| CN | 102458526 A | 5/2012 |

(Continued)

OTHER PUBLICATIONS

English Translation of Search Report Issued in Chinese Patent Application No. 20140004485 dated Apr. 18, 2014.

*Primary Examiner* — Edelmira Bosques
(74) *Attorney, Agent, or Firm* — McDonnell Boehnen Hulbert & Berghoff LLP

(57) ABSTRACT

A drug delivery device, comprises a housing having a longitudinal axis; an axially moveable component that is moveable along the longitudinal axis between a dose dialing position and a dose delivery position when a user operates the device to deliver a dose of drug; an encoder sleeve; an encoder pattern provided on the encoder sleeve, the encoder pattern comprising relatively conductive portions and relatively non-conductive portions that together comprise coded information; a contact-supporting component; and plural electrical contacts provided on the contact-supporting component. The plural electrical contacts contact the encoder (Continued)

pattern when the dose delivery button is in the dose dialing position and wherein the device is configured to move the contact-supporting component relative to the encoder sleeve as the axially moveable component moves from the dose dialing position to the dose delivery position such as to move the electrical contacts into positions where they do not contact the encoder pattern.

14 Claims, 29 Drawing Sheets

(51) Int. Cl.
*A61M 5/31* (2006.01)
*G01D 5/252* (2006.01)

(52) U.S. Cl.
CPC .... *A61M 5/31551* (2013.01); *A61M 5/31566* (2013.01); *A61M 5/31513* (2013.01); *A61M 2005/3126* (2013.01); *A61M 2005/3131* (2013.01); *A61M 2205/3306* (2013.01); *A61M 2205/3317* (2013.01); *G01D 5/252* (2013.01)

(58) Field of Classification Search
USPC ........................................................ 604/211
See application file for complete search history.

(56) References Cited

U.S. PATENT DOCUMENTS

| | | |
|---|---|---|
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 9,125,993 B2 | 9/2015 | Plumptre |
| 9,186,465 B2 | 11/2015 | Jorgenwsen et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0123829 A1 | 5/2007 | Atterbury et al. |
| 2009/0076460 A1 | 3/2009 | Nielsen et al. |
| 2009/0275916 A1 | 11/2009 | Harms et al. |
| 2011/0181301 A1 | 7/2011 | Nielsen et al. |
| 2011/0270214 A1 | 11/2011 | Jorgensen et al. |

FOREIGN PATENT DOCUMENTS

| | | |
|---|---|---|
| EP | 0937471 A2 | 8/1999 |
| EP | 0937476 A2 | 8/1999 |
| WO | 9938554 A1 | 8/1999 |
| WO | 0110484 A1 | 2/2001 |
| WO | 2006120182 A1 | 11/2006 |
| WO | 2012/140097 A2 | 10/2012 |
| WO | 2013004844 A1 | 1/2013 |

PEN TYPE DRUG INJECTION DEVICE WITH FRICTION REDUCING DOSE ENCODER MECHANISM

CROSS REFERENCE TO RELATED APPLICATIONS

The present application is a U.S. National Phase Application pursuant to 35 U.S.C. § 371 of International Application No. PCT/EP2014/050461 filed Jan. 13, 2014, which claims priority to European Patent Application No. 13151364.0 filed Jan. 15, 2013. The entire disclosure contents of these applications are herewith incorporated by reference into the present application.

FIELD OF INVENTION

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

The invention provides a drug delivery device, comprising:
  a housing having a longitudinal axis;
  an axially moveable component that is moveable along the longitudinal axis between a dose dialing position and a dose delivery position when a user operates the device to deliver a dose of drug;
  an encoder sleeve;
  an encoder pattern provided on the encoder sleeve, the encoder pattern comprising relatively conductive portions and relatively non-conductive portions that together comprise coded information;
  a contact-supporting component; and
  plural electrical contacts provided on the contact-supporting component,
  wherein the plural electrical contacts contact the encoder pattern when the dose delivery button is in the dose dialing position and wherein the device is configured to move the contact-supporting component relative to the encoder sleeve as the axially moveable component moves from the dose dialing position to the dose delivery position such as to move the electrical contacts into positions where they do not contact the encoder pattern.

By moving the electrical contacts into positions where they do not contact the encoder pattern when in the dose delivery position, frictional resistance is avoided. This reduces the force required to deliver a dose. However, it allows the dialed dose to be determined during the dialing mode and after delivery using the contacts and the encoder pattern.

Moreover, all of this is achieved without requiring provision of a mechanism in
which the encoder sleeve moves helically relative to the housing during dose dialing
but does not move helically during dose delivery; instead the mechanism may allow
the encoder sleeve to move helically during dialing and during delivery.

The use of electrical contacts and an encoder pattern has advantages compared to the
use of non-contact sensors in that electrical contacts can be more reliable, can reduce
costs (in that compact yet accurate and reliable non-contact sensors can be relatively
expensive), and in that a more compact arrangement may be achievable.

The axially moveable component may be a grip sleeve that is external to the housing, may be rotationally fixed relative to the housing and may be axially moveable relative to the housing. The use of a grip sleeve in this way provides a relatively simple and reliable arrangement. However, the grip sleeve may be omitted if a button sleeve is used for instance.

The contacts may be provided on a contact sleeve and extend through windows in an intermediate sleeve to contact the encoder pattern when the device is in the dose dialing position and may not extend through the windows in the intermediate sleeve to contact the encoder patter when the device is in the dose delivery position. This allows the contacts to be moved from the encoder pattern during delivery. The device may be configured to move the intermediate sleeve relative to the contact sleeve as the device moves from the dose dialing position to the device is in the dose delivery position. The device may be configured to rotate the intermediate sleeve relative to the contact sleeve as the device moves from the dose dialing position to the dose delivery position. Alternatively, the device may be configured to move the intermediate sleeve axially relative to the contact sleeve as the device moves from the dose dialing position to the dose delivery position. The device may be configured to move the contact-supporting component relative to the encoder sleeve as the axially moveable component moves from the dose dialing position to the dose delivery position such as to move the electrical contacts into positions where they do not contact the encoder pattern as the device moves from the dose dialing position to the dose delivery position.

The encoder sleeve may be a button sleeve that is axially constrained with the dose delivery button and that is configured to travel on two different axially separated helixes in dialing and dispensing modes respectively. This provides an alternative to the use of a grip sleeve. Use of such a device may be easier for a user than one involving a grip sleeve. The device may be configured such that the plural electrical contacts move from the encoder pattern down a ramp surface as the mode of the device changes from dialing mode to dose delivery mode. This allows the contacts to be moved from the encoder pattern during delivery.

As the device is moved from the dialing mode to the delivery mode, the plural electrical contacts may slide down the ramp surface into a recess.

Additionally, a spring may be configured to be compressed as the device is moved from the dialing mode to the delivery mode and to cause the plural electrical contacts to slide up the ramp surface after pressure is released from the dose delivery button. This allows the contacts to be moved back onto the encoder pattern after delivery.

The device may comprise an intermediate sleeve rotationally fixed relative to the housing and including thread features that engage with thread features of a button sleeve that is axially constrained with the dose delivery button. The contact-supporting component may comprise a split contact sleeve provided with ramp surfaces, the device comprising a ramp feature on the intermediate sleeve that contact the ramp surfaces of the contact sleeve. This allows the contacts to be moved from the encoder pattern during delivery.

A spring may be compressed when a user presses the dose delivery button to move the button sleeve and the intermediate sleeve such that the ramp surfaces act against the ramp feature to force first and second portions of the contact sleeves apart.

BRIEF DESCRIPTION OF THE DRAWINGS

Embodiments will now be described, by way of example only, with reference to the accompanying drawings, in which.

DETAILED DESCRIPTION

Figure 1:
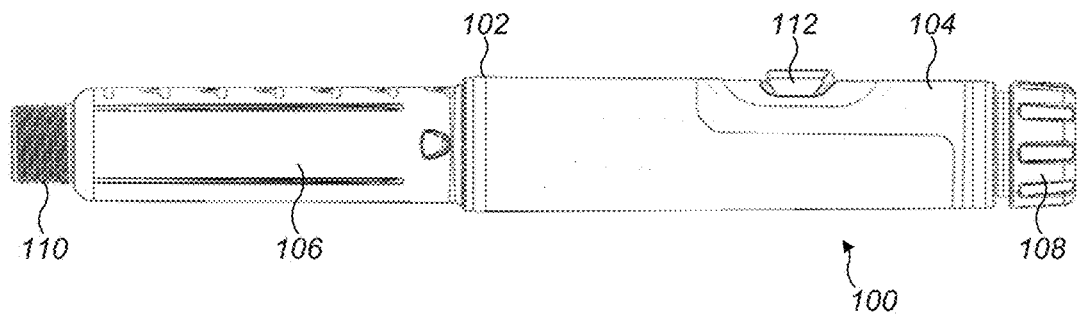
FIG. 1 shows an external view of a drug delivery device 100 suitable for implementing the present invention.

Referring firstly to FIG. 1, an external view of a drug delivery device 100 according to various embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way that the drug cartridge is permanently contained within the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a dose delivery button (416 in FIG. 3) which must be depressed in order to deliver the set drug dose. Alternatively, the rotatable dial 108 may double as a dose delivery button (as in the first to sixth embodiments described below). The display 112 may be configured to display information concerning the drug dose which has been set and/or delivered. The display 112 may further show additional information, such as the actual time, the time of the last usage/injection, a remaining battery capacity, one or more warning signs indicating that a dialed dose has not been fully dispensed, and/or the like.

Figure 2:
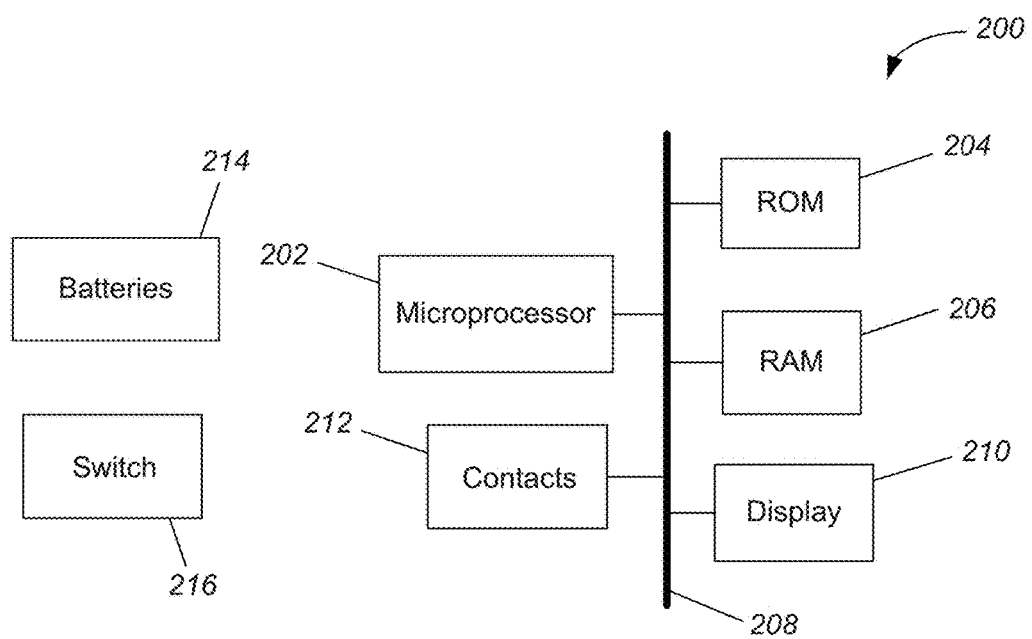
FIG. 2 shows a schematic diagram of some of the electronic components present in the drug delivery device 100 of FIG. 1.

Referring now to FIG. 2, a schematic diagram of electrical circuitry 200 forming part of the drug delivery device 100 is shown. The circuitry 200 comprises a processor 202, a non-volatile memory such as a ROM 204, a writable non-volatile memory such as flash memory 205, a volatile memory such as a RAM 206, a display 210, contacts 212 (described later on as contacts 212a-212i) and a bus 208 connecting each of these components. The circuitry 200 also comprises batteries 214 or some other suitable source of power for providing power to each of the components and a switch 216, described in greater detail below.

The circuitry 200 may be integral with the device 100. Alternatively, the circuitry 200 may be contained within an electronic module that can be attached to the device 100. In addition, the circuitry 200 may comprise additional sensors, such as optical or acoustical sensors. The circuitry 200 may comprise an audible alarm (not shown) which the processor 202 may control to sound an alarm when a dialed dose has not been fully dispensed.

The ROM 204 may be configured to store software and/or firmware. This software/firmware may control operations of the processor 202. The processor 202 utilises RAM 206 to execute the software/firmware stored in the ROM to control operation of the display 210. As such the processor 202 may also comprise a display driver. The processor 202 utilises the flash memory 205 to store determined amounts of dose dialed and/or determined amounts of dose dispensed, as will be described in more detail below.

The batteries 214 may provide power for each of the components including the contacts 212. The supply of electricity to the contacts 212 may be controlled by the processor 202. The processor 202 may receive signals from the contacts 212 and so could determine when the contacts are energised, and is configured to interpret these signals. Information may be provided on the display 210 at suitable times by operation of the software/firmware and the processor 202. This information may include measurements determined from the signals received by the processor 202 from the contacts 212.

A number of contacts 212 may be present in the device 100, as is described below.

Figure 3:
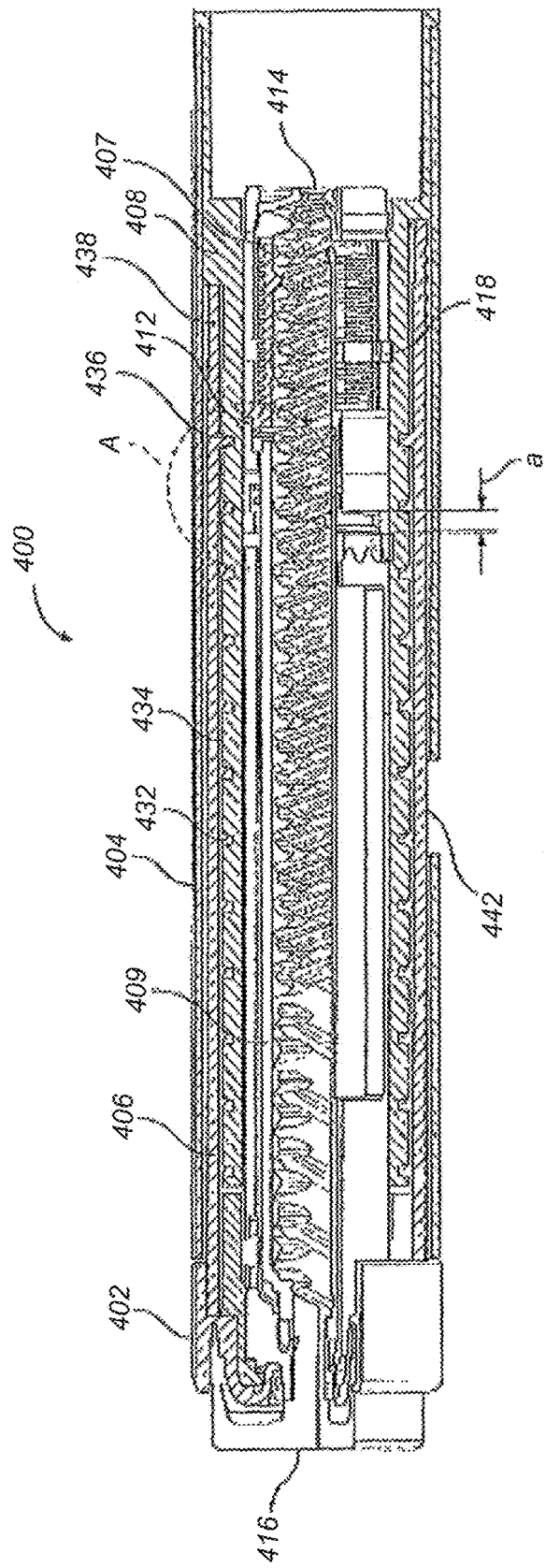
FIG. 3 shows a dose setting mechanism 400 of a drug delivery device 100 suitable for use with the invention.
Figure 4:
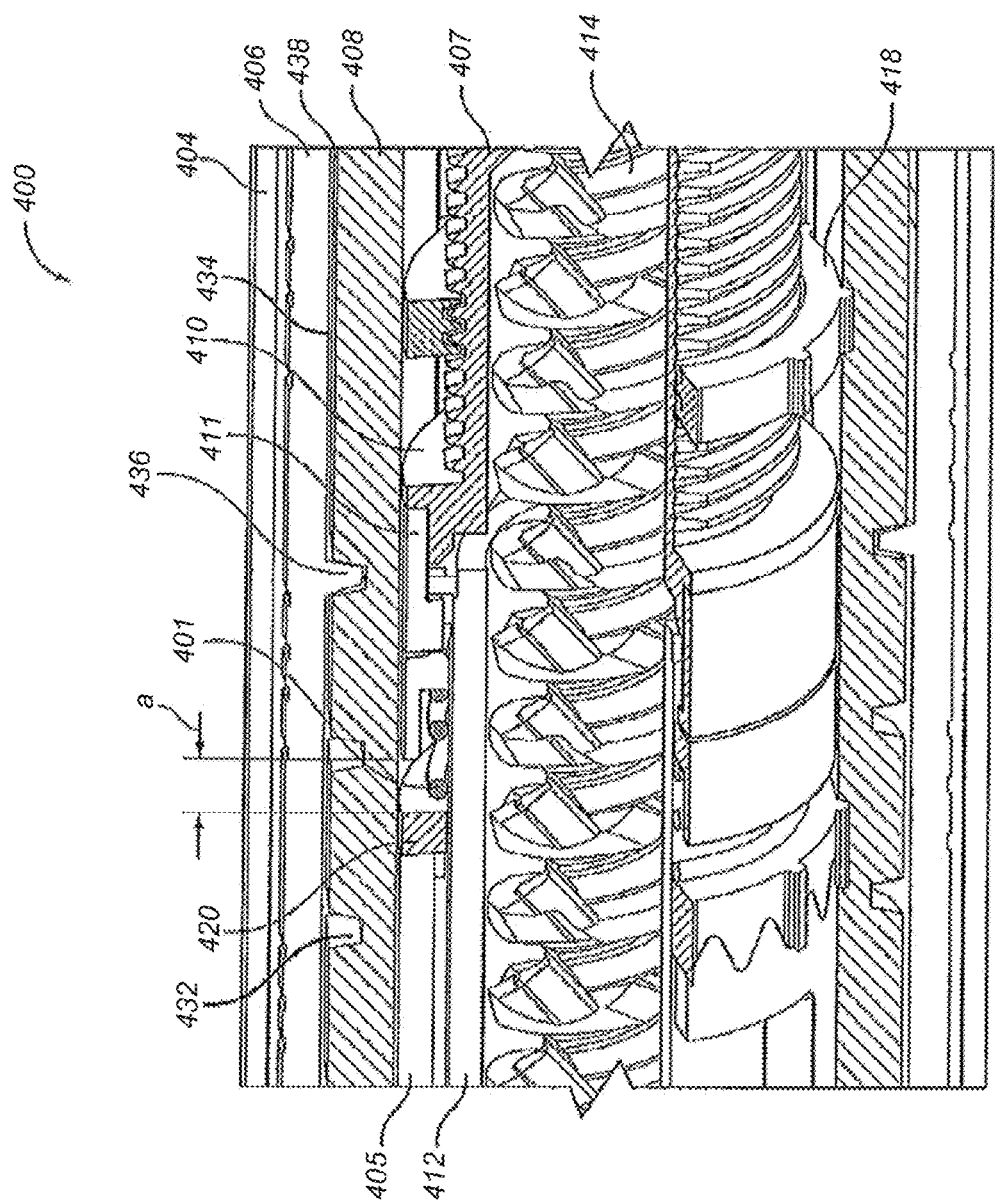
FIG. 4 shows detail of the dose setting mechanism 400 of FIG. 3.
Figure 5:
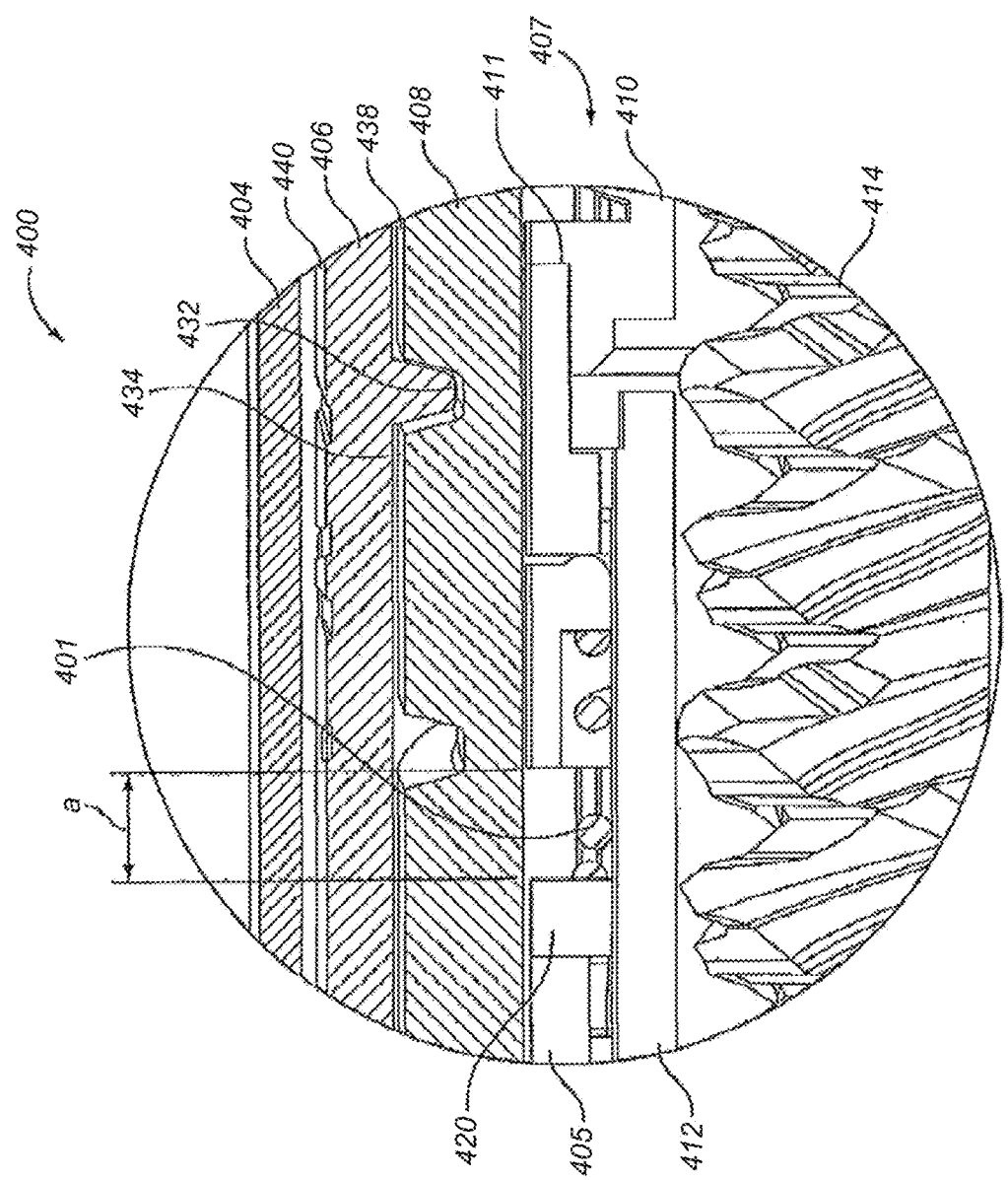
FIG. 5 shows a close up of the region marked 'A' in FIG. 3.

A fuller explanation of the operation of the dose setting and delivery mechanism supported within the first housing part 104 will now be given with reference to FIGS. 3 to 6. FIG. 3 is a cross-sectional view of a dose setting mechanism 400 of a drug delivery device 100. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and a rotatable sleeve 406. The rotatable sleeve 406 is an example of a sleeve. The inner housing 408 is an example of a body component. These components are hollow cylinders arranged concentrically. The rotatable sleeve 406 is disposed between the outer and inner housings 404, 408.

The inner housing 408 comprises a groove 432 provided along an external surface 434 of the inner housing 408. A groove guide 436 provided on an inner surface 438 of the rotatable sleeve 406 is rotatably engaged with this groove 432.

A dose dial grip 402 is located at a proximal end of the outer housing 404. The dose dial grip 402 is disposed about an outer surface of a proximal end of the rotatable sleeve 406. An outer diameter of the dose dial grip 402 preferably corresponds to the outer diameter of the outer housing 404. The dose dial grip 402 is secured to the rotatable sleeve 406 to prevent relative movement between these two components. The dose dial grip 402 is represented in the external view of FIG. 1 by the rotatable dial 108. The dose dial grip 402 supports a dose delivery button dose delivery button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle. Each groove form is effectively continuous over a number of turns. Each groove of the spindle may engage either a non-continuous helical groove form on a body portion or on a driver. Either or both a non-continuous thread formed on a body and a driver may consist of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. The first driver portion 407 may comprise a first component part 410 and a second component part 411. Alternatively, the first driver portion 407 may be an integral component part.

With the dose setting mechanism 400, as a user dials a dose with the dose dial grip 402, the metal spring 401 is selected to be strong enough to maintain engagement of both clutched couplings: the clutched coupling between the clutch 405 and the rotatable sleeve 406 and clutched coupling between the first driver portion 407 and second driver portion 412. The rotatable sleeve 406 is coupled to the dose dial grip 402 such that when a user rotates the dose dial grip 402, the rotatable sleeve 406 also rotates. As the rotatable sleeve 406 is rotated in a first rotational direction, it moves axially in a proximal direction due to its threaded connection to the inner housing 408.

This threaded connection includes a thread feature 436 on the rotatable sleeve 406 and a thread feature 432 on the inner housing 408. These are best viewed in FIG. 4. In FIG. 4, the thread feature 436 on the rotatable sleeve 406 is male (the groove guide) and the thread feature 432 on the inner housing 408 is female (the groove), although alternatively both thread features 432, 436 may be male or the thread feature 436 may be female and the thread feature 432 may be male.

When the drug delivery device is being dispensed, the user applies an axial load to the dose delivery button dose delivery button 416 located at the proximal end of the mechanism 400. The dose delivery button dose delivery button 416 is axially coupled to the clutch 405 and this prevents relative axial movement. Therefore, the clutch 405 moves axially towards the cartridge end or the distal end of the dose setting mechanism 400. This movement disengages the clutch 405 from the rotatable sleeve 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose delivery button dose delivery button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
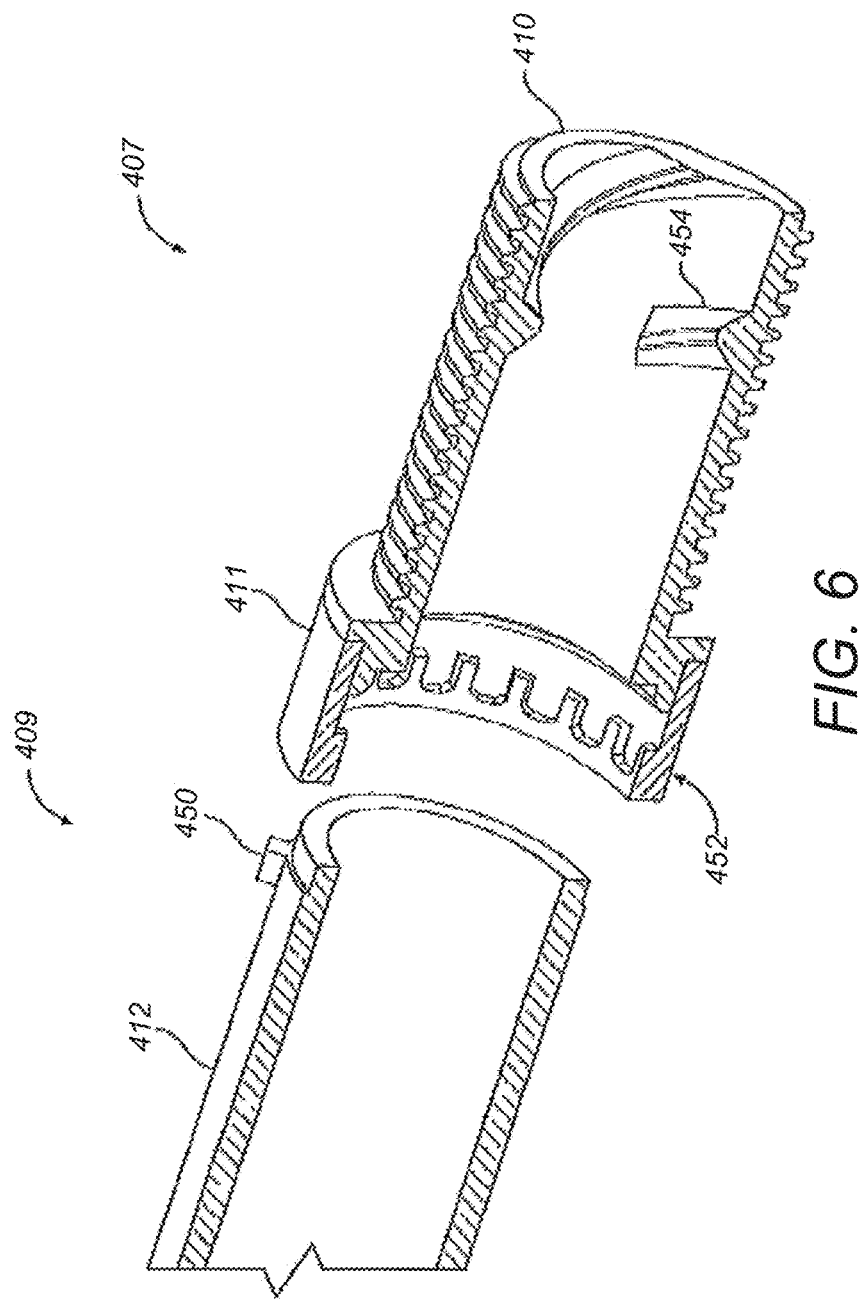
FIG. 6 is an exploded view showing details of a driver forming part of the dose setting mechanism 400 of FIGS. 3 to 5.

FIG. 6 shows in detail a first arrangement of the first driver portion 407 and the second driver portion 412 illustrated in FIGS. 3 to 5. As illustrated in FIG. 6, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove, which is easier to manufacture than a complete helical groove.

One advantage of this dose setting mechanism 400 utilizing the inner housing 408 is that the inner housing 408 can be made from an engineering plastic that minimizes friction relative to the rotatable sleeve 406 groove guide 436 and the groove 432. For example, one such engineering plastic could comprise Acetal. However, those skilled in the art will recognise that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the rotatable sleeve 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the processor 202, ROM 204, flash memory 205, RAM 206, display electronics, contacts 212 and batteries 214 previously described. Alternatively, the contacts 212 may be supported at another position on the inner surface of the outer housing 404 and linked to the processor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the rotatable sleeve 406 in order to facilitate a determination of the rotational position of the rotatable sleeve 406, as will be described in more detail below.

The dose setting mechanism 400 illustrated in FIGS. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is decoupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually decouple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the rotatable sleeve 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the rotatable sleeve 406. As a consequence, the rotatable sleeve 406 cannot rotate relative to the inner housing 404. If the rotatable sleeve 406 is prevented from rotating then, as the spindle 414 is retracted back into the dose setting mechanism 400 and thereby re-set, there will be no risk of the rotatable sleeve 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver portion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the rotatable sleeve 406 and for implementing the present invention. It will be apparent to the skilled person that other mechanisms may also be suitable.

In view of the foregoing it will be appreciated that a user twists the rotatable dial 108 to select an amount of dose to be dispensed from a drug cartridge. This causes the rotatable sleeve 406 to rotate and translate axially (longitudinally) relative to the housing 102 in a helical motion. By analysing information that relates to rotation of the rotatable sleeve 406 the extent of rotation of the dial 108, and thus the dose dialled, can be determined. Furthermore, a user presses the dose delivery button 416 to dispense an amount of dose from within a drug cartridge. Pressing the dose delivery button 416 causes the rotatable sleeve 406 to rotate and move axially (move helically) the other way. Thus by analysing information that relates to rotation of the rotatable sleeve 406, the dose dispensed can also be determined.

A helical track 300 provides a conductive pattern formed on the cylindrical outside surface of the encoder sleeve 406. One possible way of determining dialed dose that is not an embodiment of this invention is as follows. Electrical contacts 212 mounted relative to the main housing 102 are caused to contact different parts of the pattern as the encoder sleeve 406 moves helically within the main housing as a dose is dialed in and as a dose is delivered. By examining signals provided at the contacts by connection (or no connection) with the pattern on the helical track 300, the location of the encoder sleeve 406 within the main housing might be determined, or at least estimated.

Embodiments of the present invention propose a different scheme. In brief, electrical contacts 212 are caused to contact different parts of the pattern on a helical track 300 as an encoder sleeve 406 moves helically within the main housing as a dose is dialed. However, the contacts 212 are caused to move away from the helical track 300 as the device moves from dose dialing mode to dose delivery mode. The contacts 212 are kept separated from the helical track 300 during dose delivery, and are returned to contact the helical track 300 again when the device again enters dose dialing mode. By examining signals provided at the contacts by connection (or no connection) with the pattern on the helical track 300, the location of the encoder sleeve 406 within the main housing might be determined, or at least estimated, but only during dialing mode and not during the dose delivery mode. The dose delivered during the delivery mode can be calculated from the location of the encoder sleeve 406 before and after dose delivery mode. Apparatus so constructed can allow determination of the position of the encoder sleeve 406 without the contacts and helical track 300 providing resistance to axial movement during dose delivery. In schemes where contacts electrically contact a conductive pattern formed on the sleeve during dialing and delivery, conversely, friction forces resulting from contacts sliding over the conductive pattern as the sleeves rotates on the inner body can provide significant additional resistance to axial/helical movement of the body component relative to the sleeve during dose delivery.

First to sixth embodiments will now be described. Like reference numerals refer to like elements throughout this specification. Additionally, a feature described as being present or an effect that is described as being achieved in relation to one embodiment should be understood also to form part of all the other embodiments unless explicitly stated or unless it can be seen to be omitted/not achieved.

A first embodiment will now be described with reference to FIGS. 7 to 15.

Figure 7:
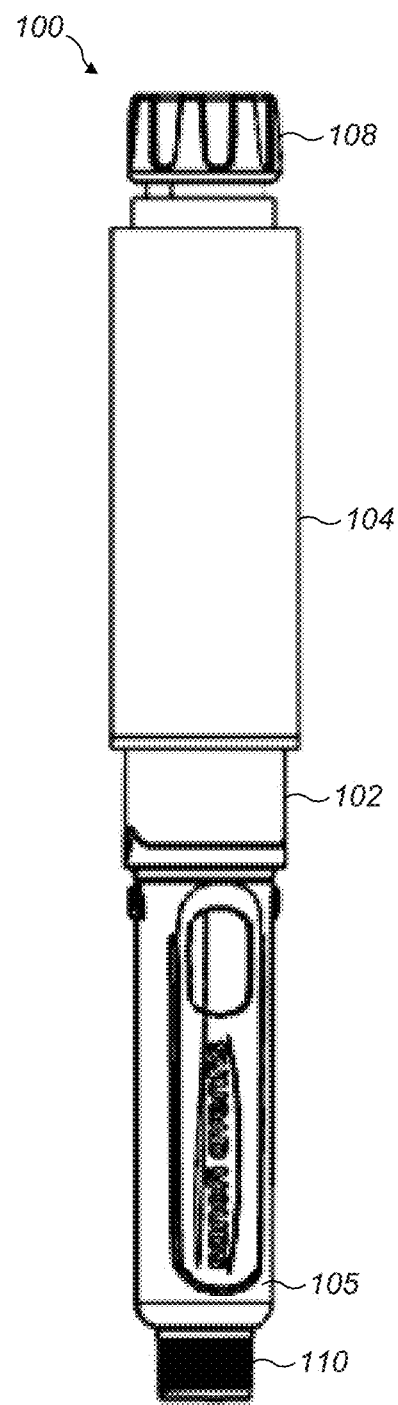
FIG. 7 is a side view of a device according to a first embodiment of the invention.
Figure 8:
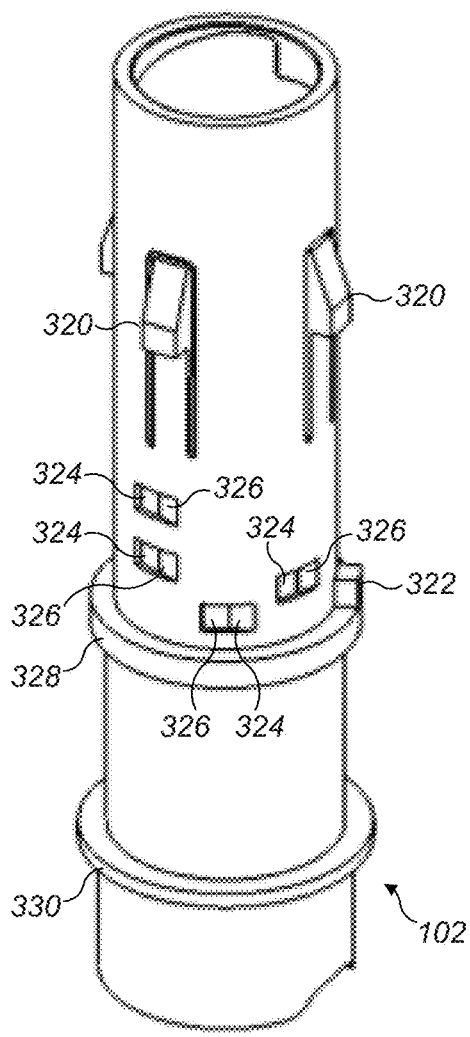
FIG. 8 is a perspective view of an outer body forming part of the device of FIG. 7 according to the first embodiment.
Figure 9:
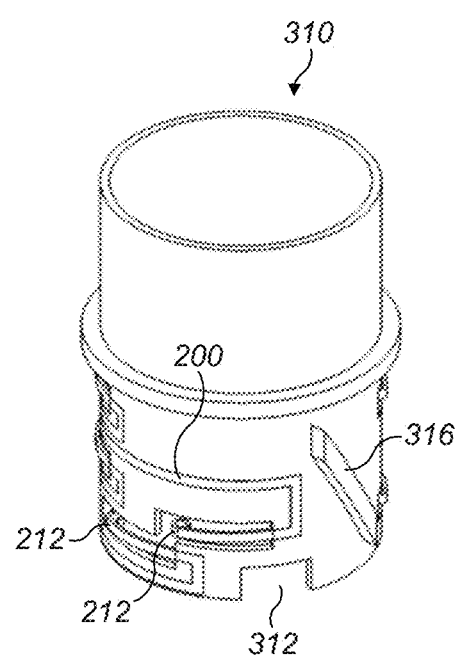
FIG. 9 is a perspective view of a sensor sleeve forming part of the device of FIG. 7 according to the first embodiment.

The injection device 100 according to the first embodiment shown in FIG. 7 includes a grip sleeve 104 as the first housing part 104. The grip sleeve 104 is configured to be able to move axially relative to the inner housing 408 but is locked in rotation, that is it is unable to move rotationally relative to the inner housing 108. The same applies relative to an outer housing part 102, which is shown in FIG. 8. A sensor sleeve 310 is shown in FIG. 9.

The outer body 102 has a generally cylindrical form. A number of features are formed on the cylindrical form of the outer body 102. These include retention clips 320. The retention clips 320 are sprung and include a ramped portion and a stop. When the sensor sleeve 310 is provided over the uppermost end of the outer body 102 shown in FIG. 8 and a force is applied to the sensor sleeve 310 in a downward direction, the retention clips 320 are resiliently biased towards the longitudinal axis of the outer body 102 as the lowermost part of the sensor sleeve 310 contacts the ramps of the retention clips 320. After the sensor sleeve 310 has moved all the way over the retention clips 320 such that the step part of the retention clips 320 is in line with the uppermost part of the sensor sleeve 310 as shown in FIG. 9, the retention clips 320 spring back to their original position, holding the sensor sleeve 310 in place. In this position, the sensor sleeve 310 is not able to move axially on the outer body 102 but is able to rotate between first and second stops. The first and second stops are provided by a protrusion 322 at the lowermost part of the outer body 102 and a notch 312 formed in the lowermost part of the sensor sleeve.

Formed within the outer body 102 are a number of windows 324. Each of these takes the form of an aperture through which contacts 212 provided on the sensor sleeve 310 can extend through the outer body 102.

Next to each window 324 is a ramp surface 326. The ramp surfaces 326 have a thickness that is lowest at the junction with the window 324 and is greatest at an opposite side thereof. As is explained below, in use a contact 212 moves from a position where it is aligned with a window 324 to slide up the ramped portion 326 such that it is no longer coincident with the window 324.

When the sensor sleeve 310 is fitted in place on the outer body 102, a lowermost surface of the sensor sleeve 310 contacts a flange 328 formed on the outer body 102.

Axial movement of the grip sleeve 104 is limited in the downwards direction by a second flange 330 that is formed on the outer body 102 and in the uppermost direction indirectly by action of the protrusion 322 within the notch 312 on the number sleeve 310 and by action of the ramp 316 against the spline 180 on the grip sleeve 104. Of course, any suitable alternative arrangement may be used instead.

Referring now to FIG. 10, the sensor sleeve 310 is shown fitted onto the outer body 102. A coil spring 314 biases and returns the grip sleeve 104.

The grip sleeve 104 is shown in wireframe in FIG. 10, so that the sensor sleeve 310 and the outer body 102 can be seen. A ramp 316 that is provided at an angle on the outer surface of the sensor sleeve 310 is visible in both FIGS. 9 and 10.

An inwardly-facing spline 180 formed on the inside surface of the grip sleeve 104 engages with the ramp 316. Biasing means (not shown), such as a torsion spring or the coil spring 314, rotationally biases the sensor sleeve 310 such that a lowermost surface of the ramp 316 as shown in FIG. 10 is always in contact with the spline 180 on the grip sleeve 104.

Figure 10A:
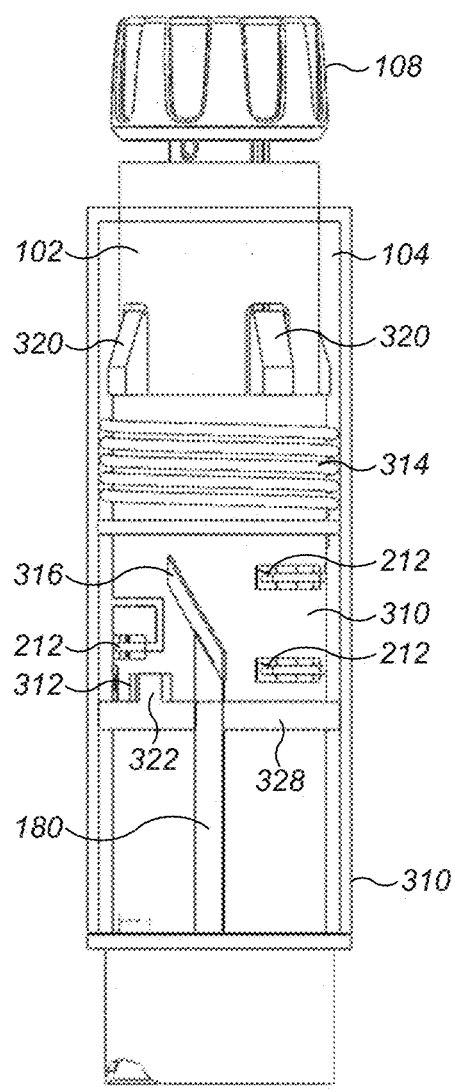
FIG. 10a is a side view of the device of FIG. 7 according to the first embodiment in a dose dialing mode.
Figure 10B:
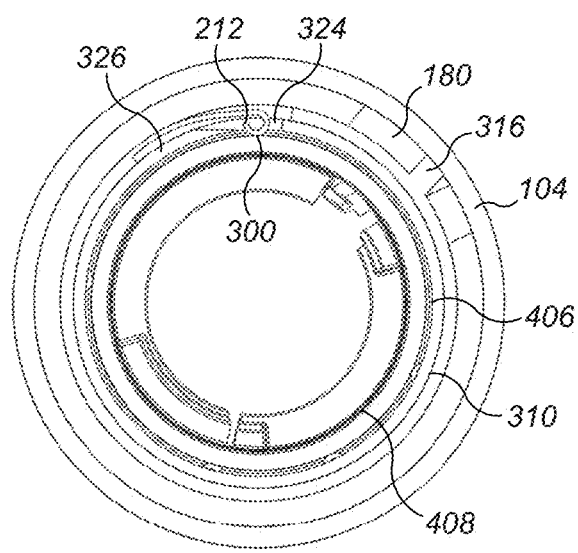
FIG. 10b is a cross-section of FIG. 10a in the dose dialing mode.

FIG. 10b shows a cross-section through the device 100, at a location that crosses both the ramp 316 and the spline 180 and is perpendicular to the page for the view shown in FIG. 10. In FIG. 10b, the ramp 316 can be seen to be in contact with the spline 180. Also, the contact 212 can be seen to extend from the sensor sleeve 310 through the window 324 in the outer body 102 to contact a helical track 300 that is provided on an outside surface of the encoder sleeve 406. The contacts 212 are resiliently biased towards the encoder sleeve 406.

The grip sleeve 104 is biased by a biasing means (not shown), for instance a spring, into the position shown in FIG. 10. The grip sleeve 104 is able to move upwards when a suitable force is applied, although it will return downwards to the position shown in FIG. 10 when the force is removed.

In use, there are two main modes of operation. The first is a dialing mode. In the dialing mode, a user may turn the rotatable dial to dial in a dose to be delivered. In a dose delivery mode, a user may grasp the device 100 in one hand and, after locating an injection needle (not shown) in a suitable body part, press the rotatable dial towards the opposite end of the device 100. As the rotatable dial 108 moves in the direction that is downwards in FIG. 10, a dose is delivered through the needle. In the dialing mode, no axial force is provided on the grip sleeve 104. As such, in the dialing mode, the grip sleeve 104 remains in the position shown in FIG. 10, which is the lowermost position.

During the dose delivery mode, or injection mode, the rotatable dial 108 and the grip sleeve 104 are subject to a force towards one another, as provided by the user. This force causes the grip sleeve 104 to move in a position that is upwards as shown in FIG. 10. As the grip sleeve 104 moves upwards, the spline 180 provides a force against the ramp 316 on the contact sleeve 310. As the contact sleeve 310 is constrained axially, the force provided by the spline 180, against the ramp 316 causes the contact sleeve 310 to rotate around the outer body 102. The rotation is anti-clockwise, which causes the ramp 316 as shown in FIG. 10 to move to the right as shown in that Figure. This causes the contacts 212 to move from a position that is coincident with the windows 312, such as to cause the contacts 212 to cease contacting the helical track 300 on the encoder sleeve 406.

Figure 10C:
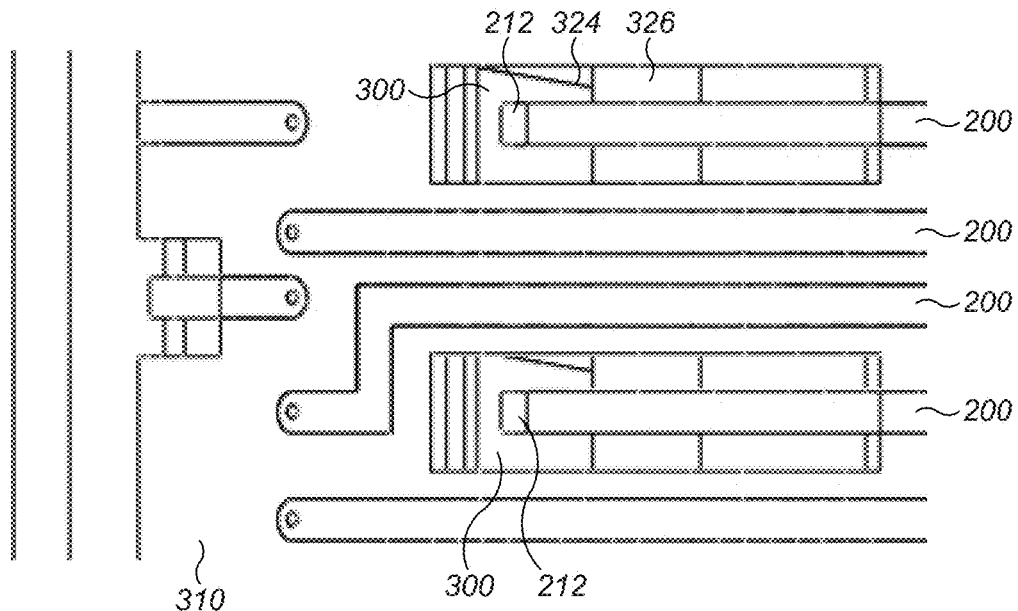
FIG. 10c shows detail of a part of the device as shown in FIG. 10a in dose dialing mode.

FIG. 10c shows the position of the contacts 212 when in the dialing mode. Here, it can be seen that the contacts 212 contact the helical track 300 through the windows 324 in the outer body 102. As the number sleeve 310 is rotated by action of the spline 180 on the ramp 316, it moves to the position shown in FIG. 11c. Here, the contacts 212 are in a fixed relationship with the contact sleeve 310, and so move along with the contact sleeve 310. As such, the contacts 212 are caused to move from the window 324 and to slide up the ramp 326 at least partly. When in the position shown in FIG. 11c, which is the position that corresponds to the grip sleeve 104 being located at the uppermost extent of its range of travel, the contacts 212 are provided on the ramp 326 and do not contact the helical track 300 through the windows 324.

After the grip sleeve 104 has moved to the uppermost extent of its range of travel, further movement of the rotatable dial 108 relative to the grip sleeve as the user continues to apply force to those components causes the rotatable dial 108 to move axially along the device 100, thereby causing delivery of medicament. Once the user reduces the force applied to the grip sleeve 104 and the rotatable dial 108, or removes that force altogether, the grip sleeve 104 is caused (by the bias arrangement) to return to the position shown in FIG. 10, which is at the lowermost extent of the range of travel of the grip sleeve 104. In this position, the contact sleeve 310 is allowed to return, and does return by virtue of the bias force, rotationally to the position shown in FIG. 10. As such, in this position the contacts 212 again coincide with the windows 324 in the outer body 102 and thus contacts the part of the helical track 300 that is behind the windows 324.

In the first embodiment, the contacts 212 are in contact with the helical track 300 during a dialing mode. As such, the processor 202 is able to determine a dose that has been dialed into the device 100 by the user through the rotatable dial 108. This is possible because the part of the helical track 300 that is coincident with the contact 212 varies according to the dose that has been dialed into the device 100 by the user through the rotatable dial 108.

As the device moves from the dialing mode to the dispensing mode, the configuration of the device 100 is such that the contacts 212 cease to contact the helical track 300. During the dispensing mode, the contacts 212 remain such that they do not contact the helical track 300. Upon the dispensing mode ending, the contacts 212 are again moved onto the helical track 300. At this stage, the processor 202 is again able to detect the helical track 300. After the device 100 has entered the dialing mode after being in the dispensing mode, the user may operate a rotatable dial 108 again, for instance to dial down any dose that is remaining (i.e. dose that has not been delivered).

The arrangement of the first embodiment is such that the processor 202 is able to detect the helical track 300 when the device is in dialing mode and is not able to detect the helical track 300 when the device is in dispensing mode. The inability of the processor 202 to monitor the dose that is currently dialed into the device during dispensing mode is not seen to be a significant problem on the basis that it is of much more interest to the user what dose is dialed into the device before delivery and also how much dose has been delivered during the delivery mode.

The helical track 300 may be configured such as to provide incremental coding. With incremental coding, the processor 202 can detect movement of the helical track 300, and, depending on the coding used, may be able to detect a direction of movement of the helical track 300, but is unable to unambiguously determine a position of the helical track without having knowledge of a dose dialed into the device immediately proceeding the current time. With incremental coding, the processor 202 may not be able to determine the position of the helical track 300 after the device has moved from the dose delivery mode to the dose dialing mode. However, by determining a number of units that are dialed between the dose delivery mode being ended and zero units being dialed into the device, the processor 202 is able to calculate (using subtraction) the number of units that were delivered during the dose delivery mode. This may be satisfactory in most implementations.

Alternatively, the helical track 300 may allow absolute encoding. In absolute encoding, the processor 202 is able to determine the location of the helical track 300, and thus the number of doses that are dialed into the device 100, without any historical context information. This can allow the processor 202 to determine the number of doses that are dialed into the device 100 at any time whilst the device is in the dose dialing mode. In these embodiments, the processor 202 may be able to determine the number of doses that were delivered during the dose delivery mode even before the user has dialed down any remaining dose, simply by subtracting the dose remaining dialed into the device after dose delivery mode from the number of doses dialed into the device before delivery mode was entered.

Further alternatively, the helical track may allow absolute encoding for a relatively short sequence, for instance 16 or 32 units, and the short sequence is then repeated a number of times to cover the full range of possible doses.

Incremental encoding, absolute encoding and hybrid incremental/absolute encoding applies to all of the first to sixth embodiments of this invention described in this specification.

Figure 11C:
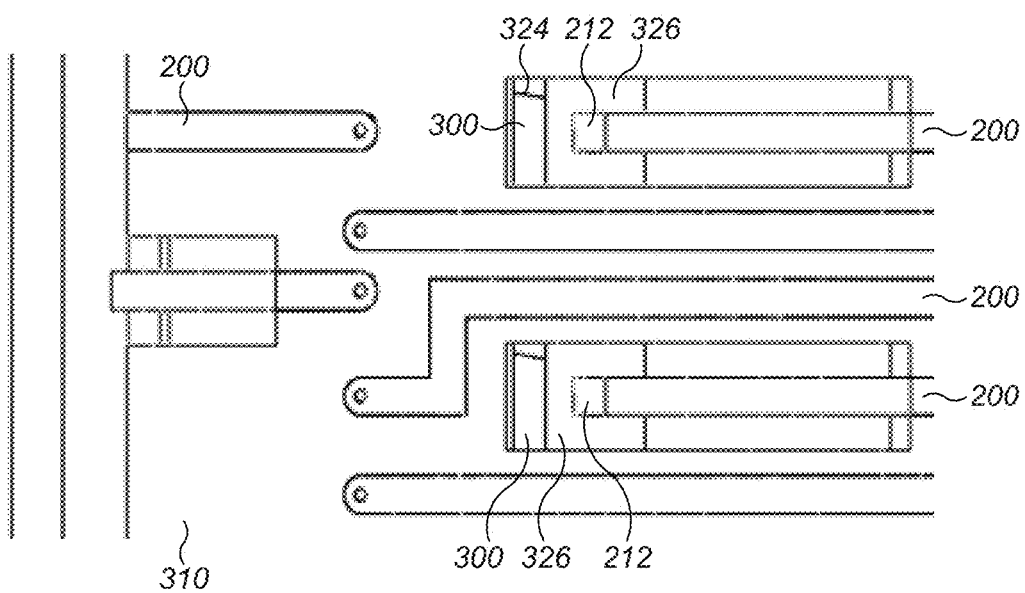
FIG. 11c is the same as FIG. 10c but relates to dose delivery mode.
Figure 11A:
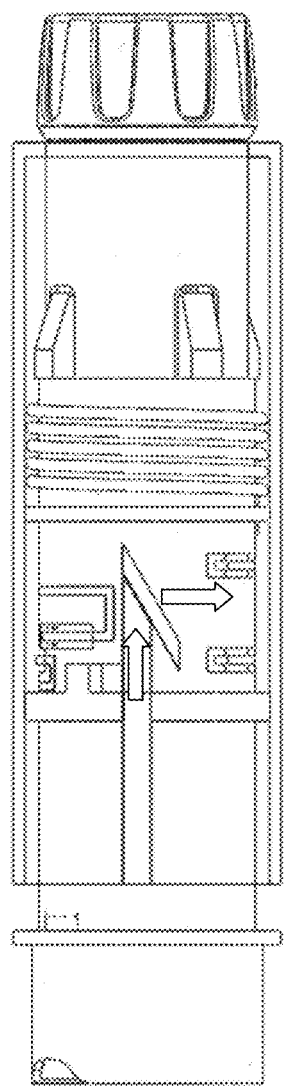
FIG. 11a is the same as FIG. 10a but relating to a dose delivery mode.
Figure 11B:
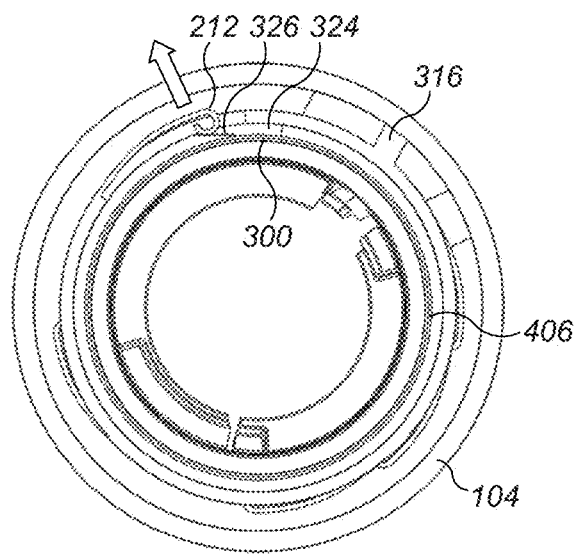
FIG. 11b is the same as FIG. 11a but relating to the dose delivery mode.

The positions of the grip sleeve 104 and the contact sleeve 310 when the device 100 is in the dose delivery mode are shown in FIGS. 11a and 11b. FIG. 11a corresponds to FIG. 10a, and is a side view with the grip sleeve 104 in wireframe. FIG. 11b is a cross section through the same location as the cross section of FIG. 10b. In FIG. 11b, the contact 212 can be clearly seen as having ridden up the ramp 326 so as not to contact the track 300 on the encoder sleeve 406.

The second embodiment will now be described with reference to FIGS. 12 to 15.

The second embodiment shares many features in common with the first embodiment, and reference numerals are re-used for like elements. The second embodiment is the same as the first embodiment described above except where explicitly mentioned in the following or where the features described in the below are inconsistent with the features of the first embodiment.

Figure 12:
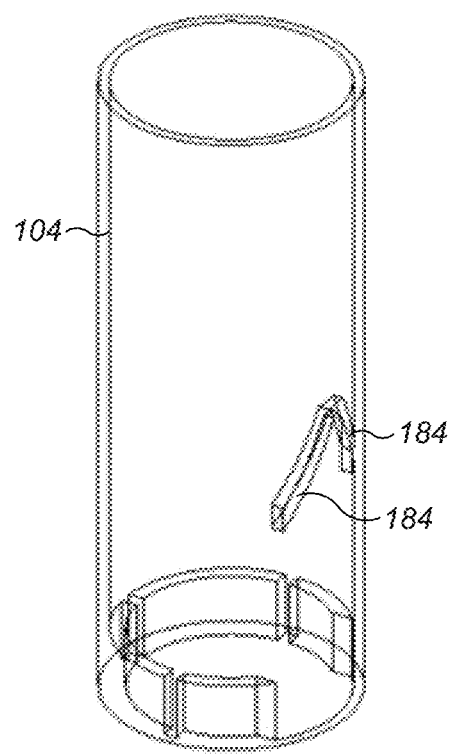
FIG. 12 is a perspective wireframe view of a grip sleeve forming part of a device according to a second embodiment of the invention.
Figure 13:
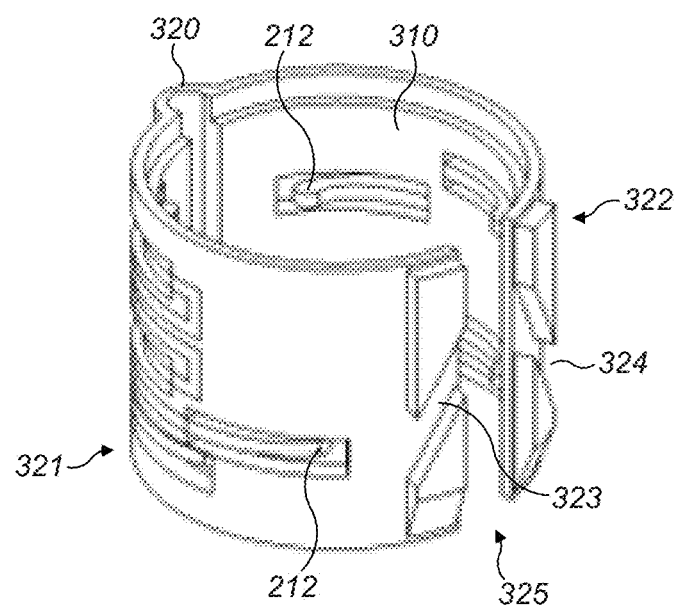
FIG. 13 is a perspective view of a sensor sleeve forming part of the second embodiment.

FIG. 12 is a wireframe perspective view of the grip sleeve 104. FIG. 13 is a perspective view of the contact sleeve 310.

The grip sleeve 104 of FIG. 12 is absent the spline 180 that is provided in the first embodiment. Instead, the grip sleeve 104 includes a first ramp 182 and a second ramp 184. The first and second ramps 182, 184 form a chevron pattern. The ramps are formed at an angle relative to the grip sleeve 104. The first ramp 102 extends upwardly from left to right as shown in FIG. 12. The second ramp 184 has the opposite configuration, and extends downwardly from left to right as shown in FIG. 12. The first and second ramps 182, 184 are formed in fixed positions on the inside surface of the grip sleeve 104.

The contact sleeve 310 does not form a complete sleeve, but instead has a gap 325 at one rotational position. Opposite the gap 325 is a live hinge 320. The gap 325 and the live hinge 320 serve to split the contact sleeve 310 into a first half 321 and a second half 322. The live hinge 320 and the gap 325 allow the first and second halves 321, 322 to move towards each other and away from each other to some extent.

Contacts 212 are formed in a resilient manner, biased inwardly with respect to the contact sleeve 310, as with the first embodiment. The live hinge 320 is arranged such as to bias the first and second halves 321, 322 of the contact sleeve 310 together.

Figure 14A:
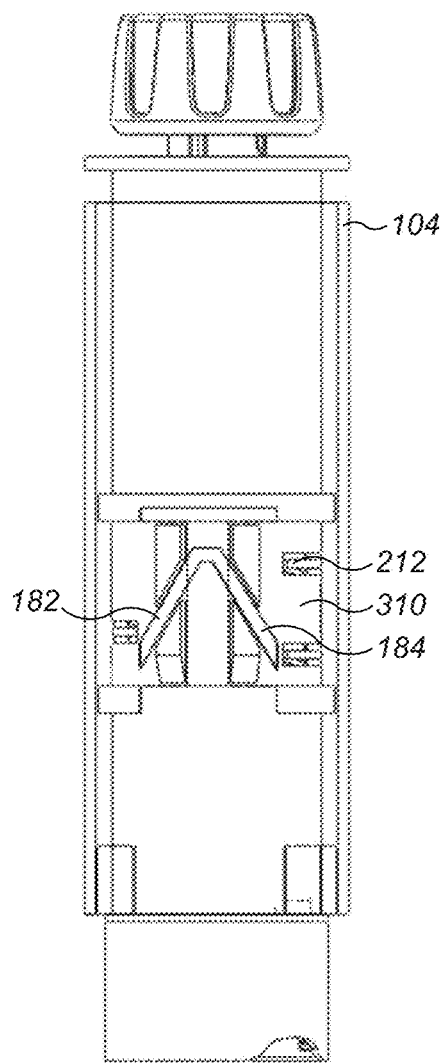
FIG. 14a is a partial side view of a device according to the second embodiment in a dose dialing mode.

After being included on the outer housing 102 and within the grip parts 104, the device 100 is as shown in FIG. 14a. Here, the grip sleeve 104 is shown in wireframe.

When installed, the first and second ramps 182, 184 are arranged to engage with first and second grooves 323, 324 that are provided on the first and second halves 321, 322 respectively of the contact sleeve 310. The first and second grooves 323, 324 are best shown in FIG. 13, but are visible also in FIG. 14*a*.

Figure 15A:
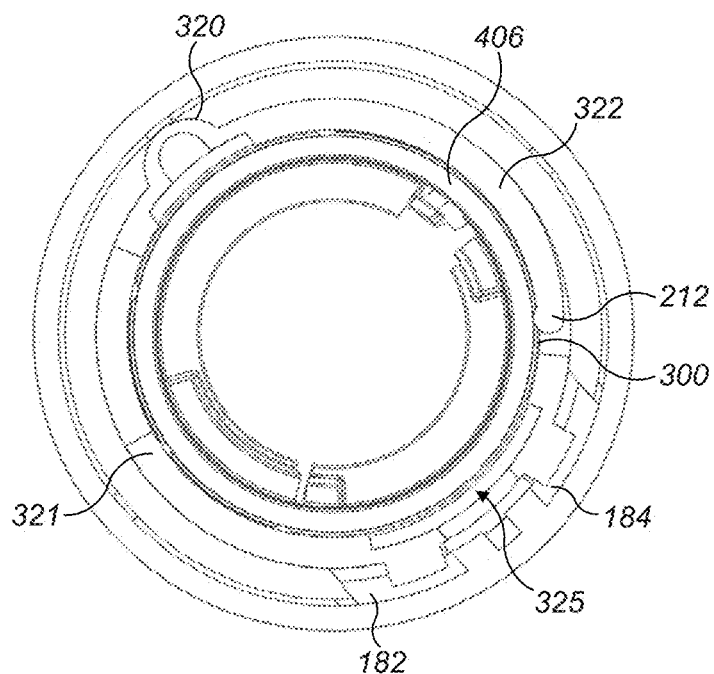
FIG. 15a is a cross-section through FIG. 14a, when the device is in dose dialing mode.

When the device is in the dialing mode, it is as shown in FIG. 14*a*. Here, the first and second ramps 182 and 184 are engaged within the first and second grooves 323, 324 respectively. The part of the ramp 182 that is within the first groove 323 is a part of the first ramp 182 that is approximately halfway along the length of the ramp. Similarly, it is a part of the second ramp 184 that is approximately halfway along the length of the ramp that is located within the second groove 323. In this position, the first and second halves 321, 322 of the contact sleeve 310 are forced together by the action of the ramps 182, 184. In this position, as is best seen in FIG. 15*a*, contacts 212 are electrically connected with the helical track 300 formed on an outside surface of the encoder sleeve 406. In the dose dialing mode, the gap 325 between the first and second halves 321, 322 of the contact sleeve 310 is at its smallest extent.

Figure 14B:
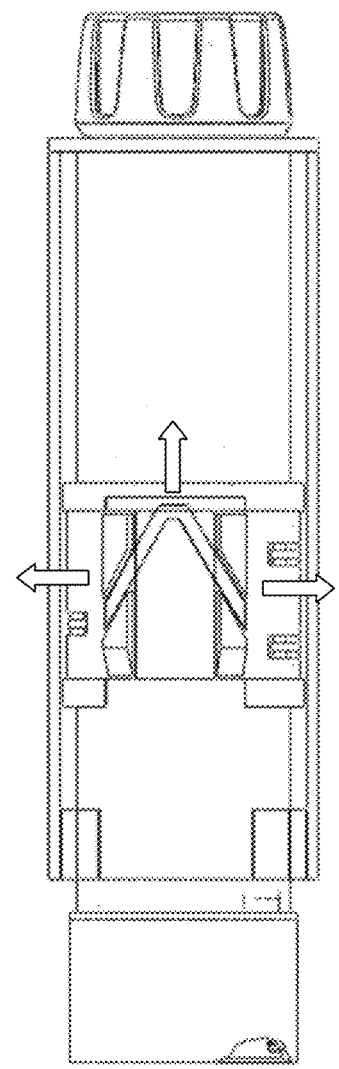
FIG. 14b is a partial side view of a device according to the second embodiment when in a dose delivery mode.
Figure 15B:
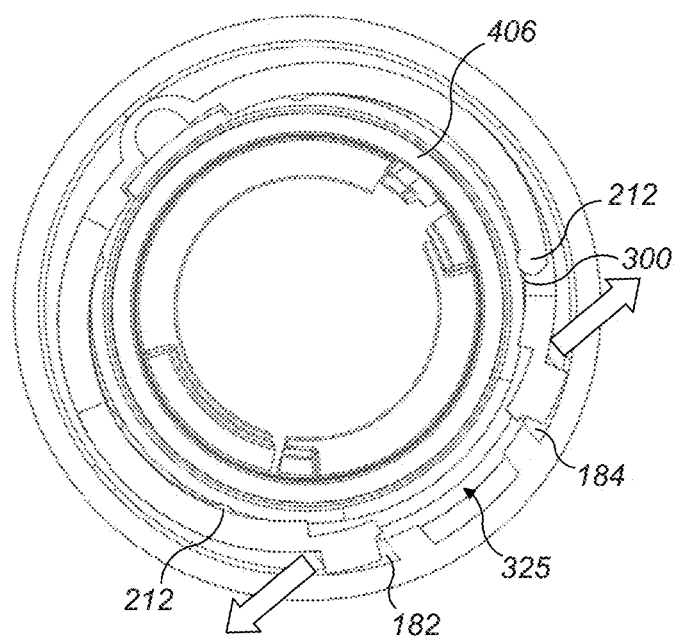
FIG. 15b is a cross-section through FIG. 14b, when the device is in dose delivery mode.

As the user applies a force such as to commence dose delivery, the grip sleeve 104 moves upwards, as is shown best in FIG. 14*b*. This movement is the same as described above with reference to the first embodiment. However, in the second embodiment the movement of the grip sleeve 104 in the upwards direction, in combination with the actual restraint of the contact sleeve 310, causes the first and second halves 321, 322 of the contact sleeve 310 to be forced apart. The result is the position shown in FIG. 14*b*, and is also shown in FIG. 15*b*. The first and second halves 321, 322 of the contact sleeve 310 are forced apart by virtue of the first and second ramp portions 182, 184 acting against the contact sleeve 310 such as to cause the ramps 182, 184 to slide within the first and second grooves 323, 324 respectively. In particular, the ramps 182, 184 move from being at a position where a particular part of their length is within their respective groove 323, 324 to a position where a part of their length that is at a greater distance from the corresponding part of the other ramp within the other groove. Since the distance is greater, the gap 325 is caused to be larger, and thus the first and second halves 321, 322 are further apart.

Consequently, the contacts 212 are moved away from the encoder sleeve 406 to the extent that the contacts 212 no longer contact the helical track 300 that is provided on the outside surface of the encoder sleeve 406, as can be seen in FIG. 15*b*.

A third embodiment will now be described with reference to FIGS. 16 to 20. The third embodiment shares features in common with the first and second embodiments, and reference numerals are re-used for like elements. The third embodiment is the same as the first and second embodiments described above except where explicitly mentioned in the following or where the features described in the below are inconsistent with the features of the above.

Figure 16:
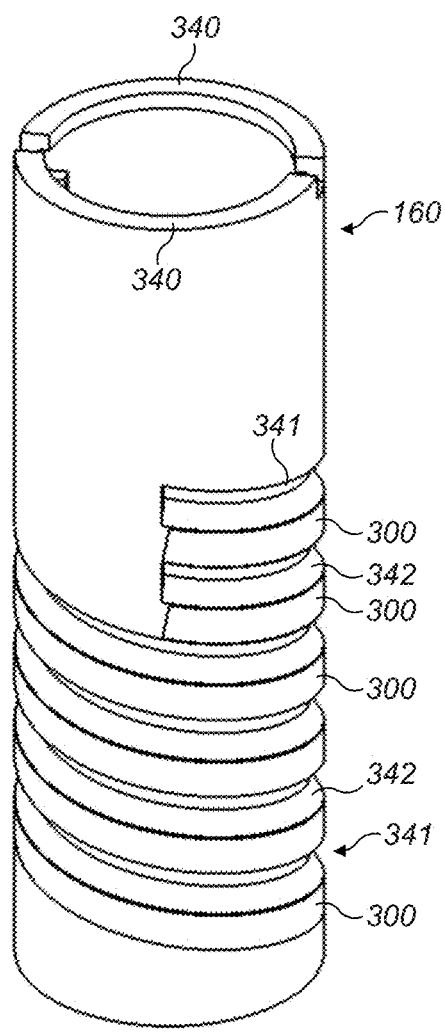
FIG. 16 is an encoder sleeve forming part of a device according to a third embodiment of the invention in perspective view.

FIG. 16 is a perspective view of a button sleeve 160. The button sleeve 160 travels on two different axially separated helixes in dialing and dispensing modes respectively. Top and bottom parts of the button sleeve 160 are generally featureless, and a central part has formed thereon some features. These comprise a helical track 300 and a recess 341 interposed between successive turns of the helical track. In this example, the helical track 300 is a twin start thread feature, so there are actually two helical tracks 300 in parallel. It may however be a single, triple or other number start track.

The helical track 300 is formed on a peak of a thread that is formed in the middle section of the button sleeve 160. The helical track 300 is formed on parts of the button sleeve 160 that are generally formed on the surface of a cylinder having as its axis the central axis of the device 100.

The helical track 300 has a width dimension, that extends vertically as shown in FIG. 16. The recess 341 provides separation between successive turns of the (twin start) helical track 300. The profile of the recess 341 is more clearly shown in FIGS. 18 and 19, which are described below.

Figure 17:
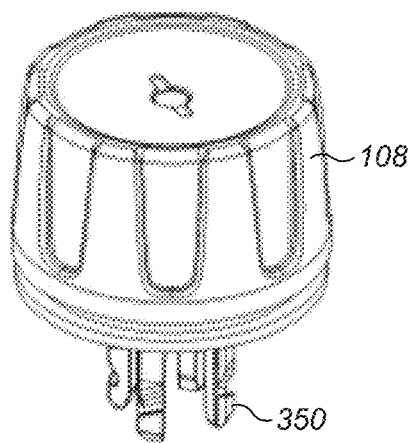
FIG. 17 is a perspective view of a rotational dial forming part of the device according to the third embodiment of the invention.

FIG. 17 is a perspective view of the rotatable dial 108. Rotatable dial clip features 350 depend from the bottom of the rotatable dial 108. These mate with encoder sleeve clip features 340, shown in FIG. 16, when the rotatable dial 108 is installed on the button sleeve 160. This is clearly shown in FIG. 18*a* and FIG. 18*b*, which are cross-sections through the vertical length of the device 100. As can be seen from FIG. 18*a*, there is some interlocking between the rotatable dial clip features 350 and the encoder sleeve clip features 340 once the device 100 is assembled. The interlocking aspect of the features 340, 350 provides for minimal or no axial movement of the rotatable dial 108 relative to the button sleeve 160. The rotatable dial 108 is able to rotate relative to the button sleeve 160, which is rotationally constrained only to the number sleeve. This is a slightly different embodiment of the core mechanism than is illustrated in and described with reference to FIGS. 3 to 6.

Figure 18A:
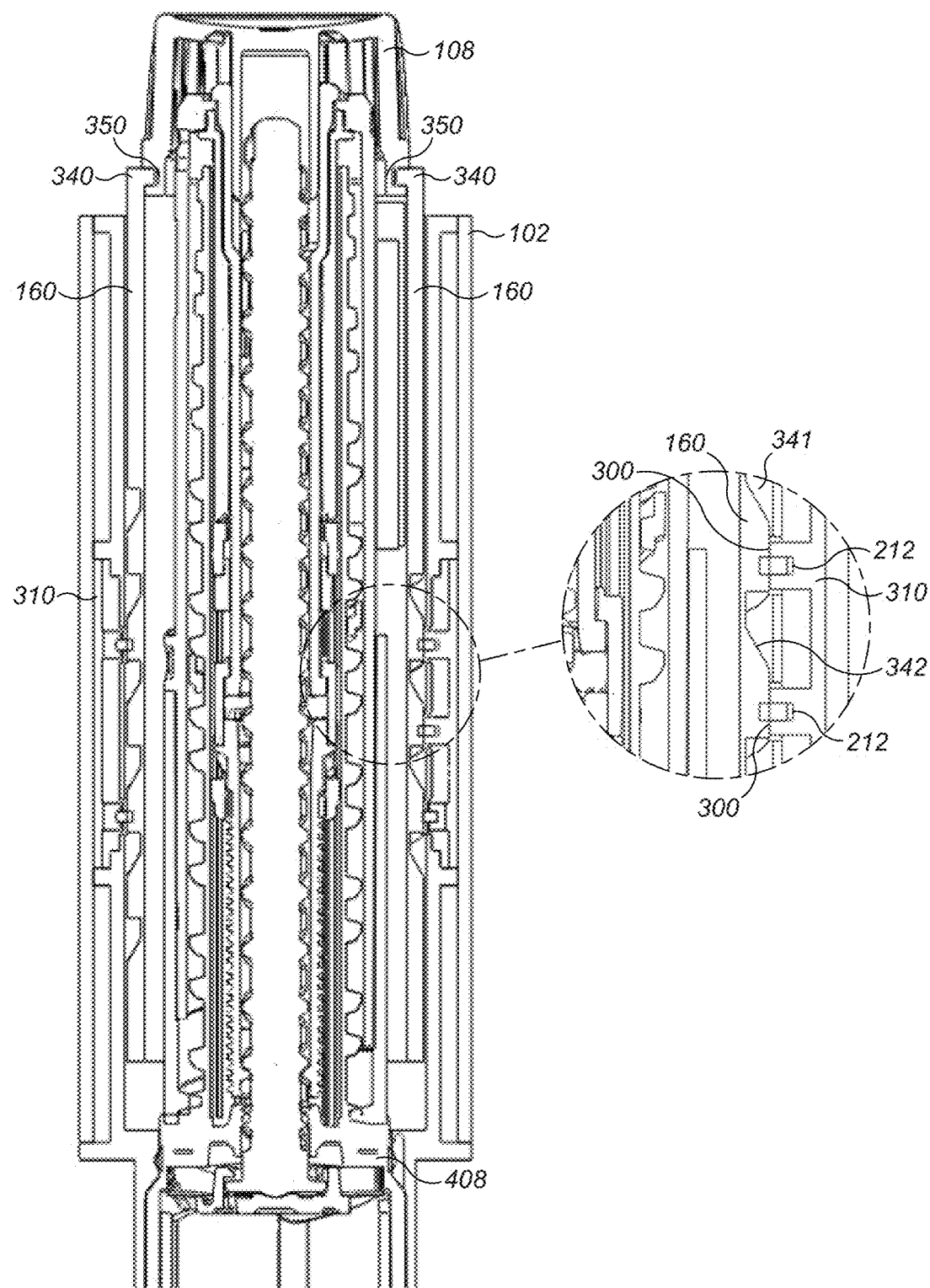
FIG. 18a is a vertical cross-section through the device according to the third embodiment of the invention when the device is in a dose dialing mode.
Figure 18B:
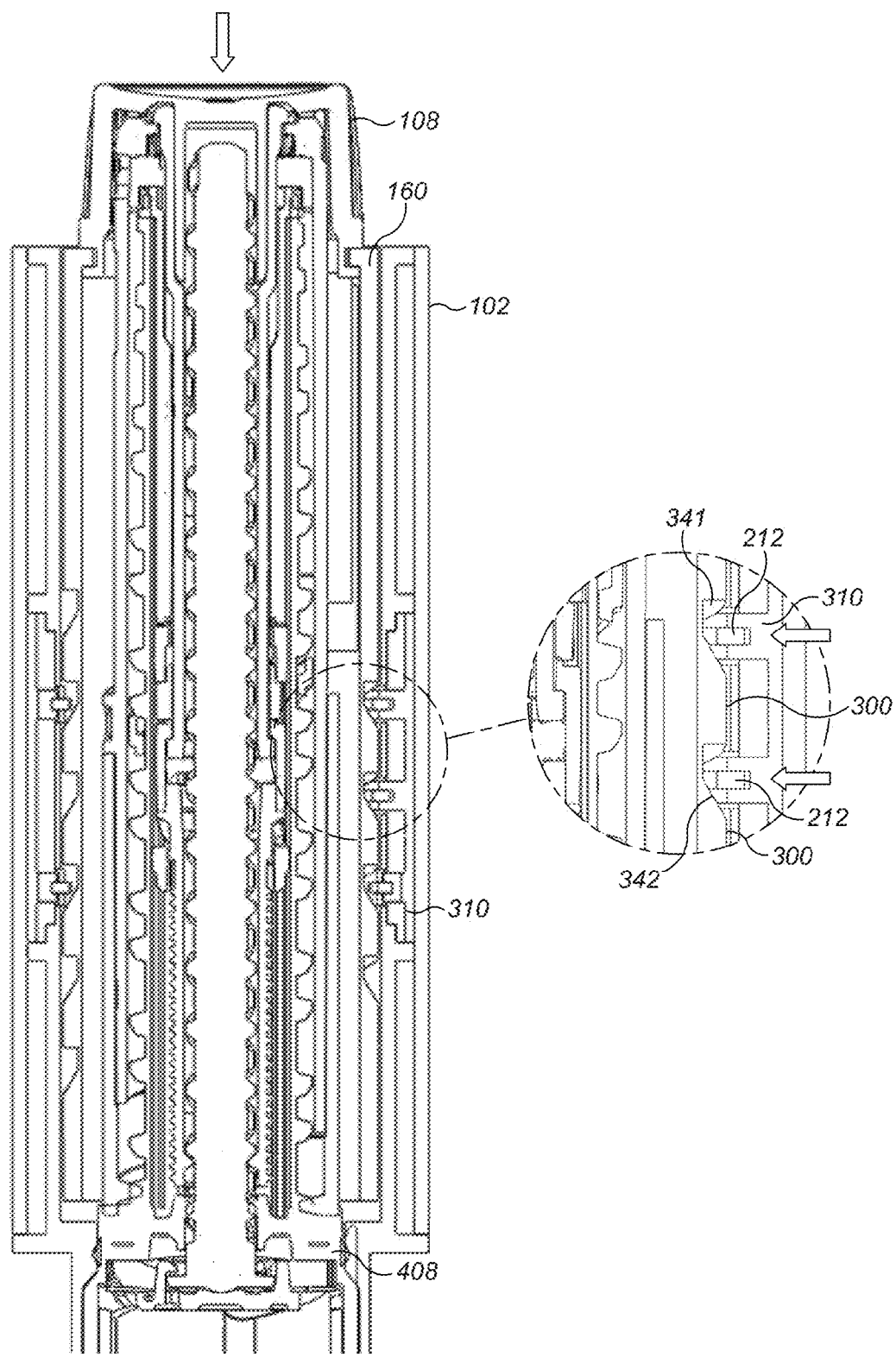
FIG. 18b is the same as FIG. 18a but relating to a dose delivery mode.
Figure 19A:
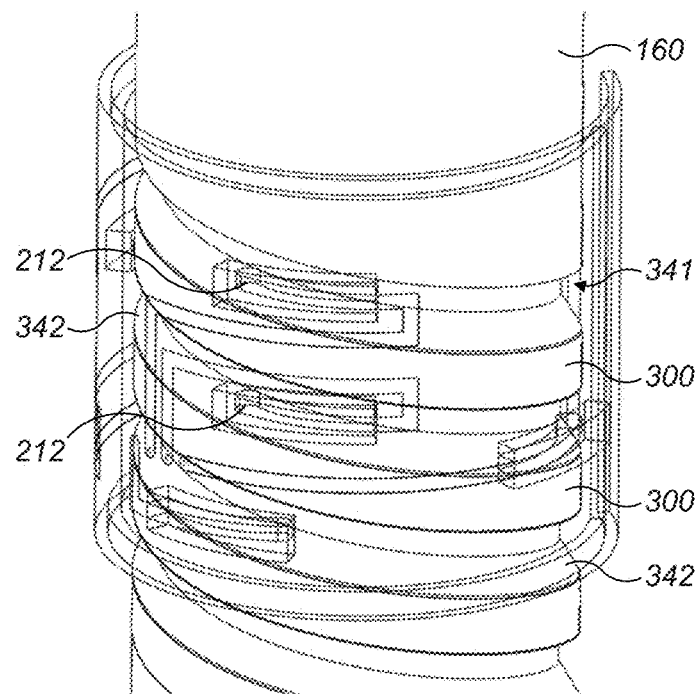
FIG. 19a is a partial perspective and partial wireframe view of the device according to the third embodiment when in a dose dialing mode.
Figure 19B:
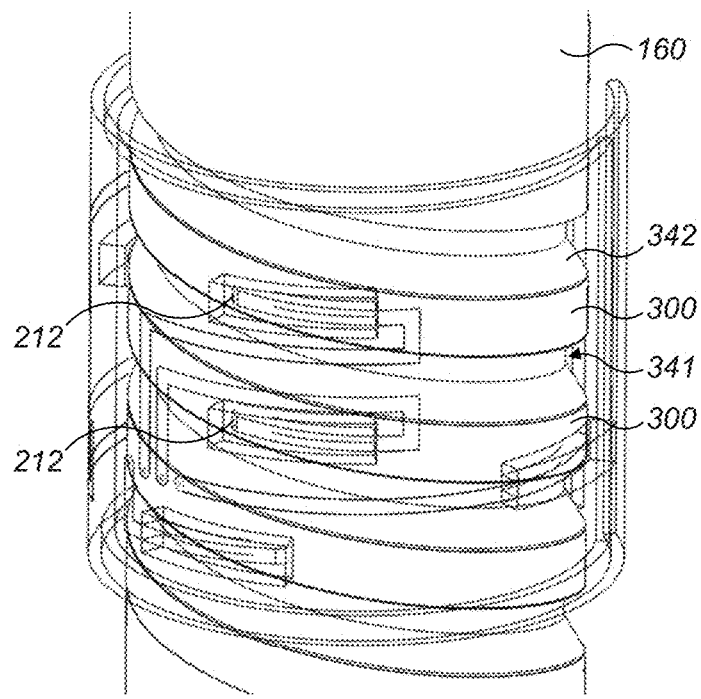
FIG. 19b is the same as FIG. 19a but relating to dose delivery mode.
Figure 20:
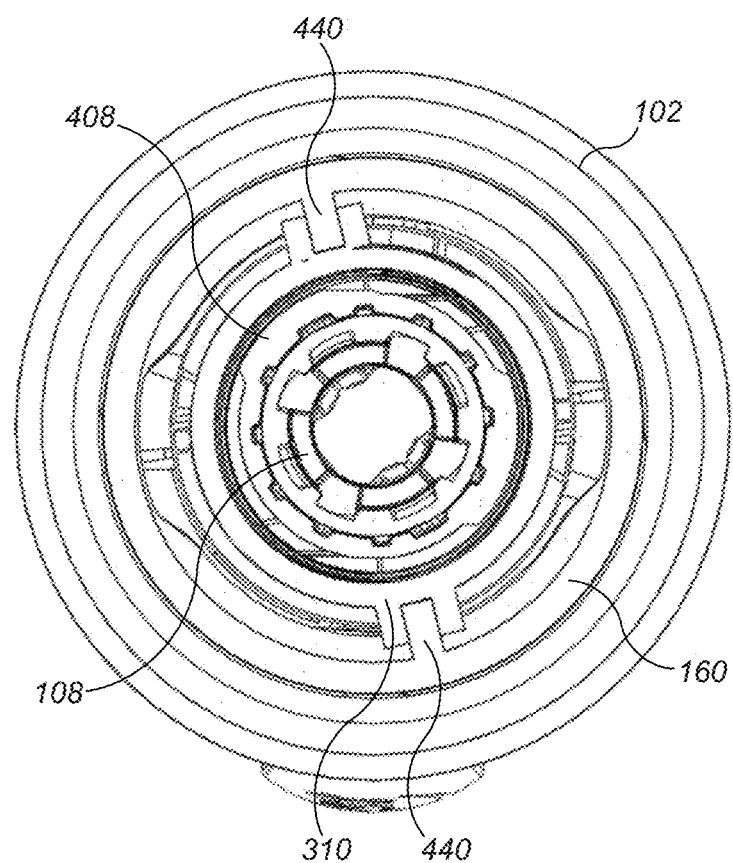
FIG. 20 is a cross-section through a device according to the third embodiment.

As is best seen in FIGS. 18*a* and 18*b*, the recesses 341 include a ramp surface 342 that extend from the peaks on which the helical tracks 300 are formed and the bottom of the recesses 341. In use, the contacts 212 move from the helical tracks 300 down the ramp surface 342 as the mode of the device 100 changes from dialing mode to dose delivery mode, as will now be described.

FIG. 18*a* shows the device in dialing mode. Here, the rotatable dial 108 is biased to the position shown in FIG. 18*a* by a spring (not shown). The contact sleeve 310 is in a fixed position relative to the inner housing 408 and the housing 102. There is no grip sleeve present in this embodiment. In the dialing mode, the contacts 212 that are supported in the contact sleeve 310 are located coincident with the helical track 300 on the button sleeve 160. This can be seen also in FIG. 19*a*. As a dose is dialed in the dialing mode, the rotatable dial 108, and thus the button sleeve 160, extends upwardly on a helical path. The pitch of the helical path is the same as the pitch of the helical tracks 300. As such, as the rotatable dial 108 is rotated by the user, the helical path 300 moves beneath the contacts 212. If the helical track 300 is an absolute encoder track, the particular part of the helical track 300 that contacts the contacts 212 at a given time is indicative of the dose that is dialed into the device 100.

To dispense a dose, a user presses the rotatable dial 108 distally, that is downwards in FIG. 18*a* and FIG. 18*b*. This compresses the spring that biases the rotatable dial 108 upwards in the dialing mode. This also displaces the button sleeve 160 distally, downwards in FIGS. 18*a* and 18*b*. The amount of travel through which the rotatable dial 108 and the button sleeve 160 move to compress the spring is limited in any suitable way. After the spring has been compressed and travel to compress the spring has stopped, further movement of the and the button sleeve 160 occurs helically, rotating the button sleeve 160 as the rotatable dial 108 extends downwards in the direction shown in FIGS. 18*a* and 18*b* (but without rotating).

As the device 100 is moved from the dialing mode to the delivery mode, the helical track 300 and the recess 341 move in a vertical position relative to the contacts 212. This causes the contacts 212 to slide down the ramped portion 342 into the recess 341. This is clearly visible in FIGS. 18*b* and 19*b*. As such, when the device is in the dose delivery mode, the contacts 212 are present in the recess 341 and are not in contact with the helical track 300. As the dose is delivered, and the button sleeve 160 rotates helically downwards as shown in FIGS. 18*a* and 18*b*, the contacts 212 are not in contact with the helical track 300. As such, there is no frictional drag between the helical track 300 and the contacts 212 as the dose is delivered.

When the user has finished delivering the dose, pressure is released from the rotatable dial 108. The spring that was compressed at the beginning of the dose delivery movement causes the rotatable dial 108 and the button sleeve 160 to move upwards in the direction shown in FIGS. 18*a* and 18*b*. This results in the contacts 212 sliding up the ramped portion 342 to again contact the helical track 300. As such, after the user has released the rotatable dial 108 after delivering a dose, the processor 202 can again determine the position of the button sleeve 160 relative to the contact sleeve 310.

When in the dose delivery mode, the contacts 212 may contact some part of the recess 341. However, the force with which the contacts 212 contact the recess 341, if at all, is significantly less than a force with which the contacts 212 contact the helical track 300 when the device 100 is in the dialing mode. As such, although there may be frictional resistance provided by the contacts 212 during the dose delivery mode, the resistance is less than would be the case were the contacts 212 contacting the helical track 300. The encoded sleeve is rotationally locked to the number sleeve by spline features 440.

A fourth embodiment will now be described with reference to FIGS. 21 to 26.

The fourth embodiment is similar to the second embodiment described above, and all of the features of that embodiment are present in this embodiment unless otherwise stated or unless the features of this embodiment are inconsistent with that embodiment.

The device 100 of the fourth embodiment is absent of a grip sleeve. Instead it includes a button sleeve 360. The button sleeve 360 has button sleeve clip features 362 at the top end thereof. These clip features 362 connect with rotatable dial clip features 350 of the rotatable dial 108, which are as shown in FIG. 17 and described above. When the device 100 is assembled, the rotatable dial 108 is axially fixed to the button sleeve 360. The button sleeve 360 also is rotationally locked to the number sleeve.

Figure 21:
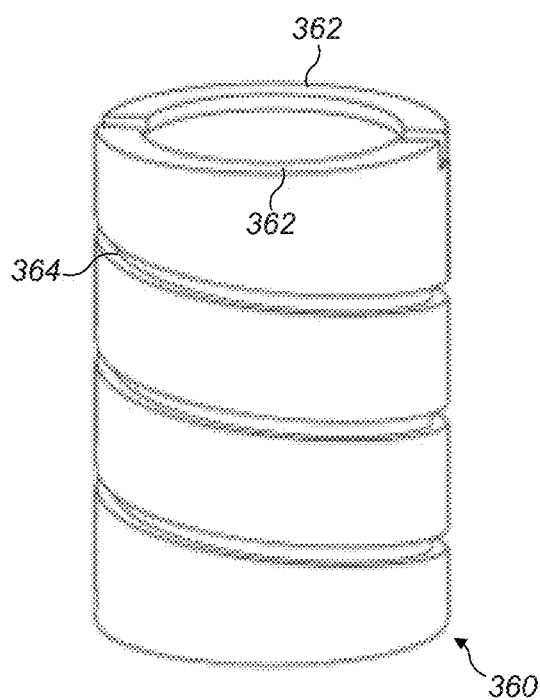
FIG. 21 is a button sleeve forming part of a device according to a fourth embodiment of the present invention, in perspective view.

A helical thread feature 364 is provided on an outer surface of the button sleeve 360. This is best seen in FIG. 21.

Figure 22:
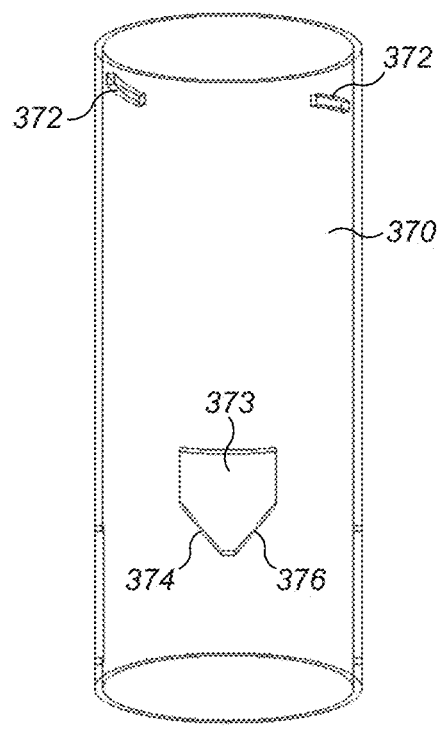
FIG. 22 is a perspective view of an intermediate sleeve forming part of the device according to the fourth embodiment of the invention.

An intermediate sleeve 370, which is best shown in FIG. 22, is provided. In use, the intermediate sleeve fits on the outside of the button sleeve 360, as is best seen from FIGS. 23 and 24. Thread features 372 of the intermediate sleeve are formed on the interior surface of the intermediate sleeve. The intermediate sleeve thread features 372 engaged with the thread features 364 of the button sleeve 360 in use. The intermediate sleeve 370 is rotationally fixed relative to the housing 102 and the inner housing 408.

Also on the interior surface of the intermediate sleeve 370 is a ramp feature 373. This has a first ramp surface 374 and a second ramp surface 376.

Figure 24A:
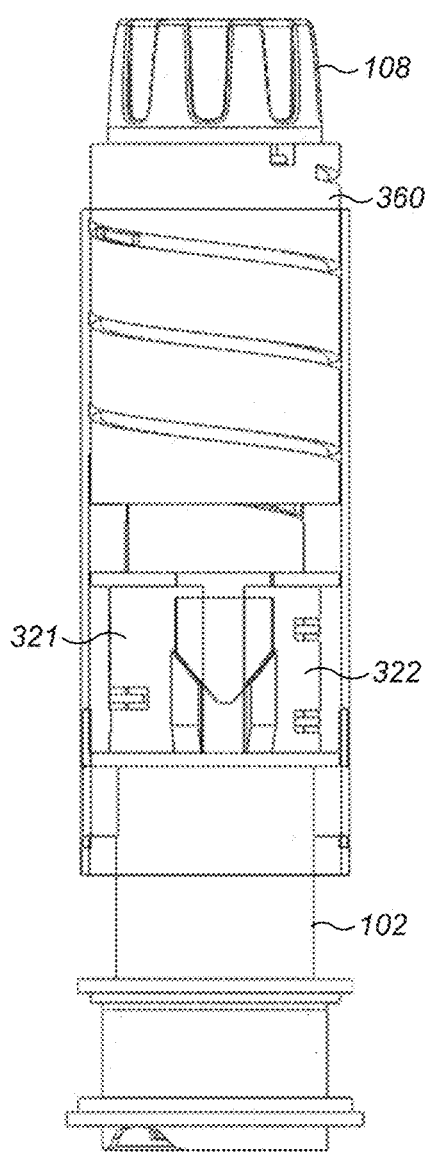
FIG. 24a is a side, partial wireframe view of the device according to the fourth embodiment when in a dose dialing mode.
Figure 24B:
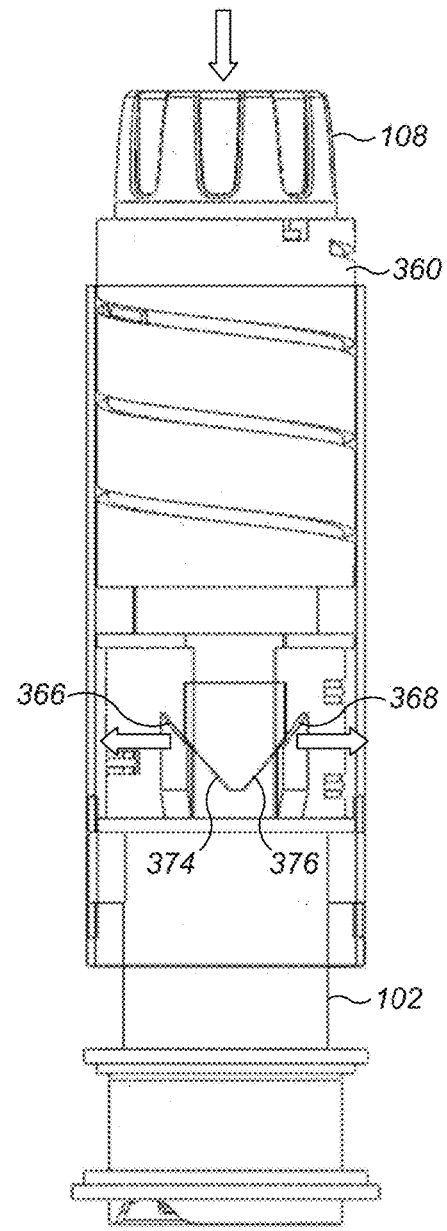
FIG. 24b is the same as FIG. 24a, but when the device is in the dose delivery mode.

A sensor sleeve 310 is substantially as described above with reference to the second embodiment. However, instead of the first and second grooves 323 and 324 of the second embodiment, the contact sleeve 310 is provided with first and second ramp surfaces 366, 368. The contact sleeve first and second ramp surfaces 366, 368 are best seen in FIG. 24*b*.

As can be seen in the Figures, the ramp surfaces 374, 376 of the intermediate sleeve corresponds to, and contact, the contact sleeve ramp surfaces 366, 368.

Figure 23:
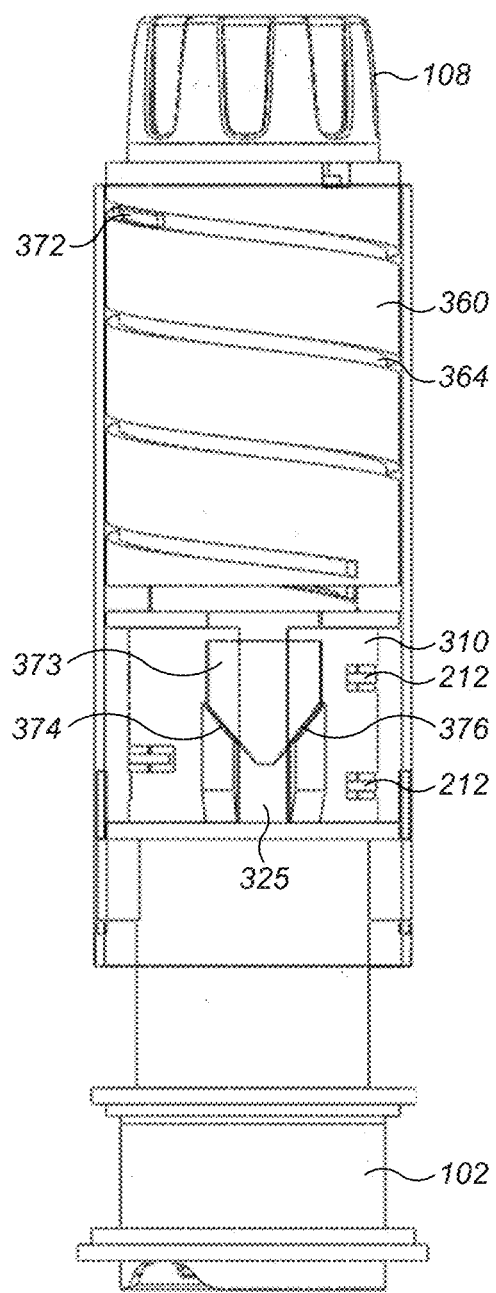
FIG. 23 is a side, partial wireframe view of the device according to the fourth embodiment of the invention.

In dialing mode, the rotatable dial 108 is biased into its most proximal position, i.e. the position shown in FIG. 23, by the spring. In the dialing mode, the intermediate sleeve 370 and the button sleeve 360 are also held in their most proximal positions, also as shown in FIG. 23.

Figure 25A:
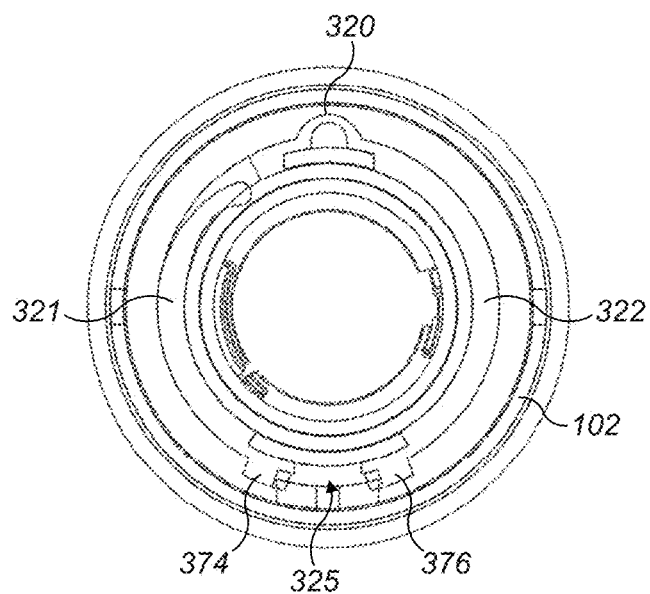
FIG. 25a is a cross-section through FIG. 24a, when the device is in the dose dialing mode.
Figure 25B:
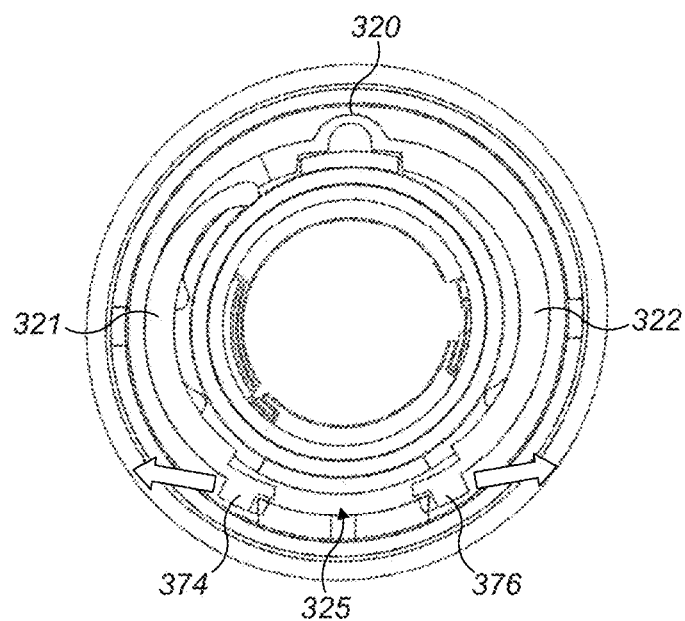
FIG. 25b is the same as FIG. 25a, but when the device is in the dose delivery mode.

When the user presses the rotatable dial 108 in a direction that is downwards in FIG. 23, in order to commence dose delivery, the rotatable dial 108 is displaced distally, that is downwards. This compresses the spring and moves the button sleeve 360, and therefore the intermediate sleeve 370, in the distal direction, which is downwards in FIG. 23. As the button sleeve 360 and the intermediate sleeve 370 move downwards, the ramp surfaces 374 and 376 of the ramp feature 373 on the intermediate sleeves 370 act against the contact sleeve ramp surfaces 366, 368 and force the first and second halves 321,322 of the contact sleeves 310 apart. The result is shown in FIGS. 24*b* and 25*b*. As for the second embodiment, the gap 325 is larger when the device 100 is in the dose delivery mode than it is when the device is in the dialing mode.

As for the second embodiment, when the first and second halves 321, 322 of the contact sleeve 310 are forced apart, contacts 212 are lifted away from the helical track 300 that is provided on the outside surface of the button sleeve 160. As such, when the device 100 is in the dose delivery mode, there is little or no friction resulting from movement of the contacts 212 relative to the helical tract 300 as the button sleeve 160 moves helically within the outer body 102.

When the user releases pressure from the rotatable dial 108 in order to cease delivering a dose, the spring forces the rotatable dial 108, and thus also the button sleeve 360 and the intermediate sleeve 370, upwards. Afterwards, the device again has the position shown in FIGS. 24*a* and 25*a*. The first and second halves 321, 322, of the contact sleeve 310 may be biased together by the live hinge 320, or may be biased together in some other way.

In a variation (not shown) of the fourth embodiment, a button sleeve 360 is used to displace a sensor sleeve like that shown in the first embodiment in order to disconnect the contacts 212 from the helical tract 300 during changing of the device from the dose dialing modes to the dose delivery mode.

The fifth embodiment will now be described with reference to FIGS. 26 to 34.

The fifth embodiment is similar to the first embodiment, except that the contacts 212 have been rotated by 90° and are now aligned with the number sleeve. The main difference between the fifth and the first embodiment is that in the fifth embodiment the change in position between the dialing mode and the dispensing mode is axial rather than rotational. All of the features of the first embodiment are present in this embodiment unless otherwise stated or unless the features of this embodiment are inconsistent with that embodiment.

Figure 26:
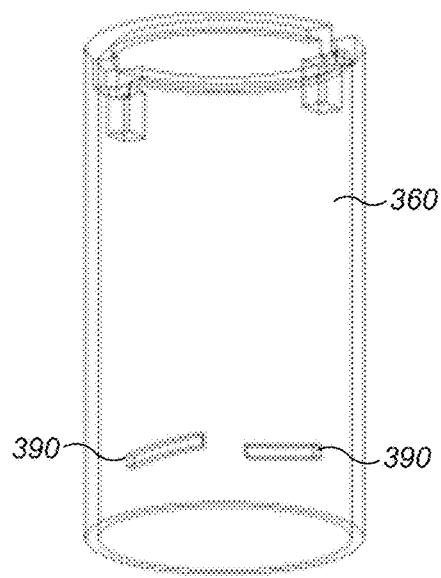
FIG. 26 is a wireframe perspective view of a button sleeve forming part of a device according to a fifth embodiment of the invention.

A button sleeve 360, which is best shown in FIG. 26, is axially locked to the rotational dial 108 and is rotationally locked to the number sleeve.

Figure 27:
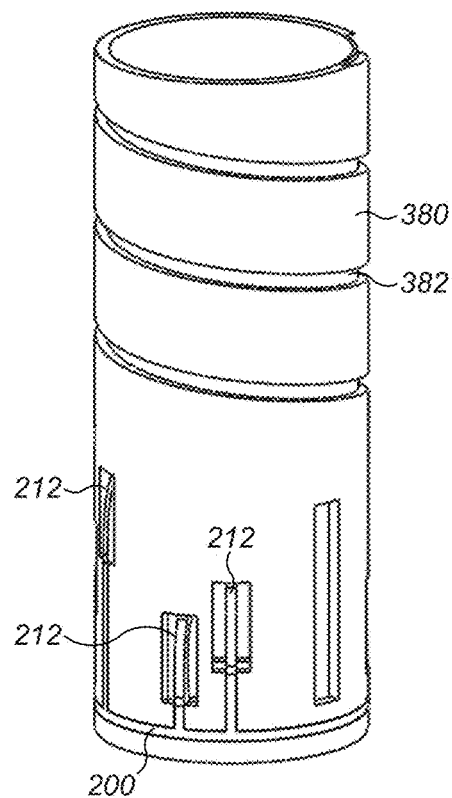
FIG. 27 is a perspective view of a sensor sleeve forming part of the device according to the fifth embodiment of the invention.

A button sleeve 380, which is best seen in FIG. 27, is provided with thread features 382 provided on the outer surface of the sensor sleeve 380. The sensor sleeve thread features 382 interact with thread features 390 that are formed on the inner surface of the button sleeve 360.

The contacts 212 are mounted on the sensor sleeve 380. The sensor sleeve 380 is rotationally fixed to the outer body 102 but is able to move axially between stops. Cut outs in the outer body 408 allow the contacts 212 to engage with the number sleeve when the device 100 is in dose dialing mode.

Figure 28:
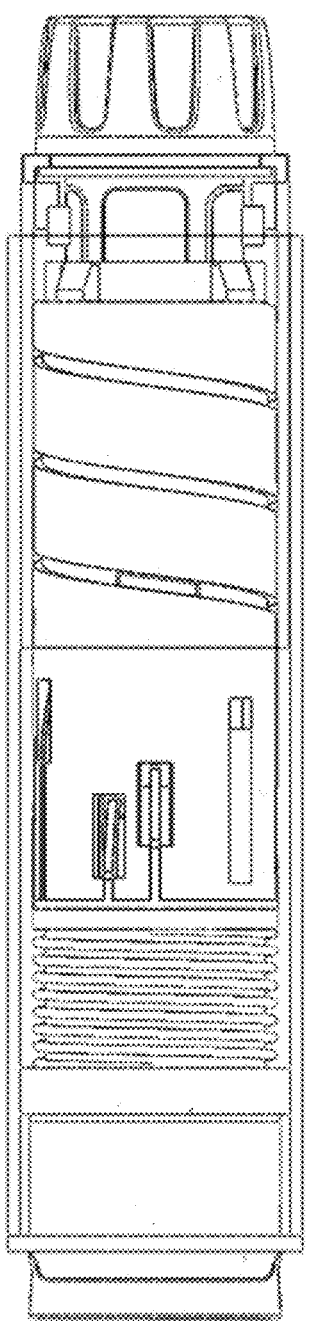
FIG. 28 is a partial side, partial wireframe view of the device according to the fifth embodiment.
Figures 29A, 29B:
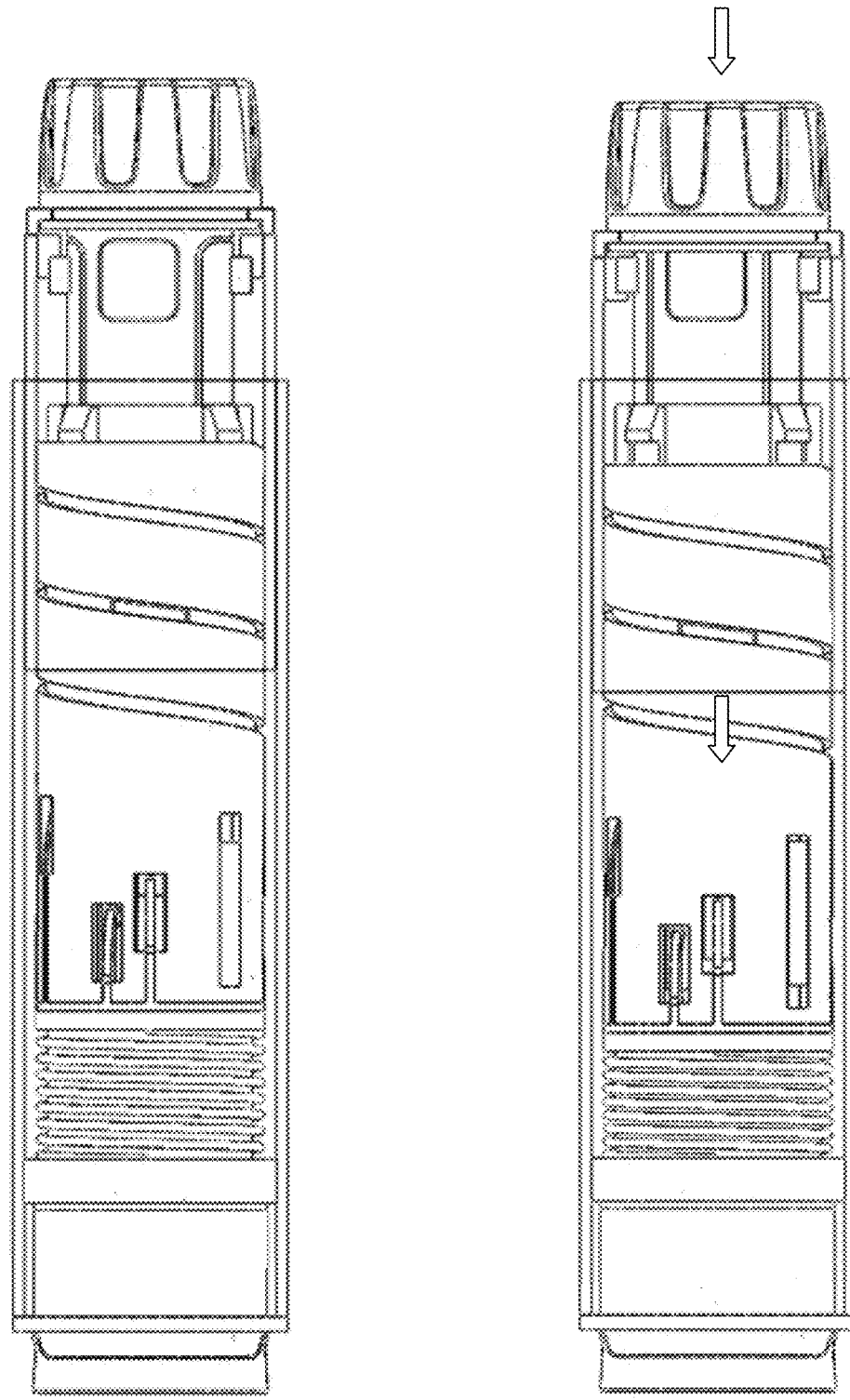
FIG. 29a is the same as FIG. 28, but showing a dose dialed into the device and showing the device in the dose dialing mode.
FIG. 29b is the same as FIG. 29a, but relates to the dose delivery mode.
Figure 30A:
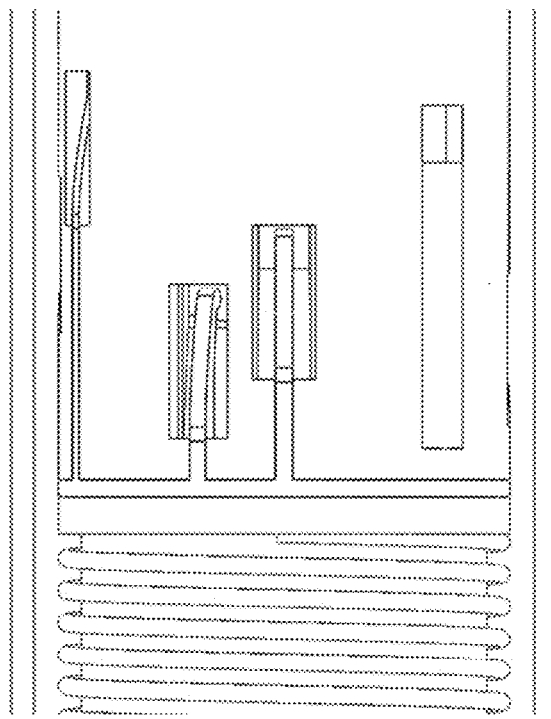
FIG. 30a is some detail of FIG. 29a, when the device is in the dose dialing mode.
Figure 30B:
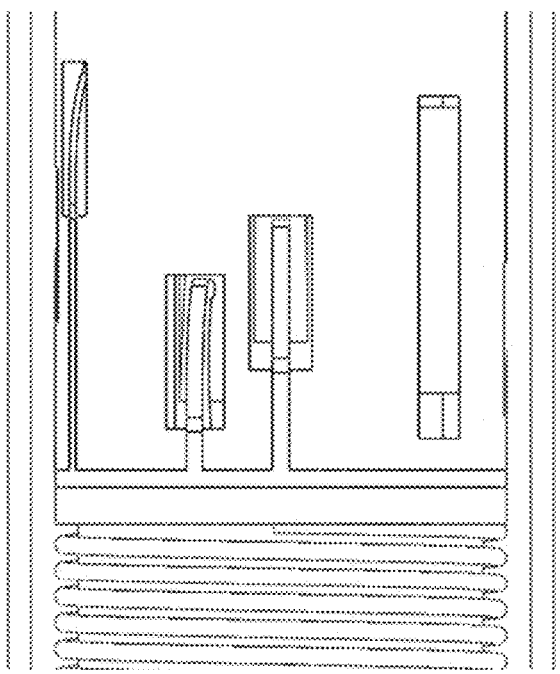
FIG. 30b is the same as FIG. 30a but relates to the dose delivery mode.

When a dose is dialed, the rotational dial 108 is held in its most proximal position by the spring. The button sleeve 360 and the sensor sleeve 380 are therefore also held in the most proximal position, as shown in FIG. 28. In this position, the contacts 212 are aligned with windows 324 in the outer body 102, allowing the contacts 212 to connect with the helical code 300 and thus allowing the processor 202 to determine the position of the number sleeve.

When the user wishes to dispense a dose, the user presses on the rotatable dial 108 downwards in the figures. This compresses the spring. This also displaces the button sleeve 360, as can be seen from FIG. 29b. The button sleeve 360 and the sensor sleeve 380 move axially with the rotatable dial 108. As this movement happens, the contacts 212 are forced up the ramp surfaces 326 that are provided on the outer body 408 such that they no longer are aligned with the windows 324 and no longer contact the helical track 300.

Figure 31:
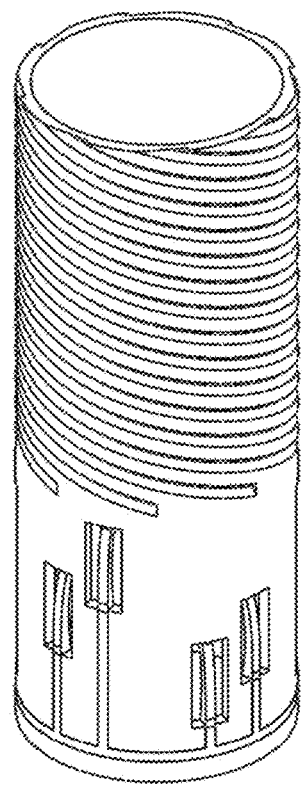
FIG. 31 is a perspective view of a contact sleeve forming part of a device according to a sixth embodiment of the invention.
Figure 32:
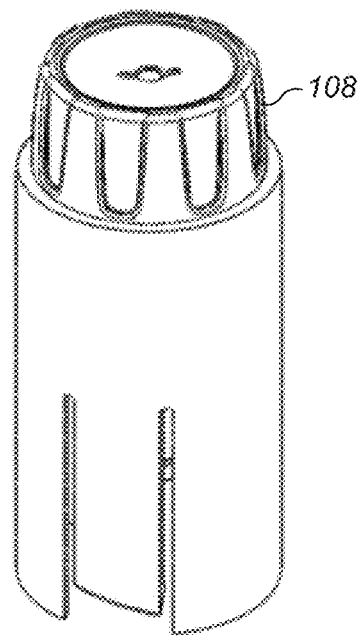
FIG. 32 is a perspective view of a rotatable dial forming part of the device according to the sixth embodiment of the invention.

A sixth embodiment will now be described with reference to FIGS. 31 to 34. The sixth embodiment is similar to the fifth embodiment. However, instead of using a button sleeve to move the sensor sleeve between the dialing and dose delivery modes, the rotatable dial 108 is extended. This is best seen in FIG. 32. Here it can be seen that the rotatable dial 108 has a sleeve portion depending from the dial parts that the user would turn in use.

In the dialing mode, the rotatable dial 108 is held in its most proximal position by a spring. The sensor sleeve 380, which is best seen in FIG. 31, is therefore also held in the most proximal position. In this position, the contacts 212 are aligned with windows 324 in the outer body 408. This allows the contacts 212 to connect with the helical pattern 300. This allows the processor 202 to determine the position of the number sleeve The number sleeve and the encoder sleeve are rotationally fixed with respect to one another. As a dose is dialed, the rotatable dial 108 moves outwardly along a helical path defined by the thread interface of the inner body. The thread on the sensor sleeve 380 has an equal pitch to the thread on the inner body, and as such the sensor sleeve 380 does not move during the dialing operation.

Figure 33A:
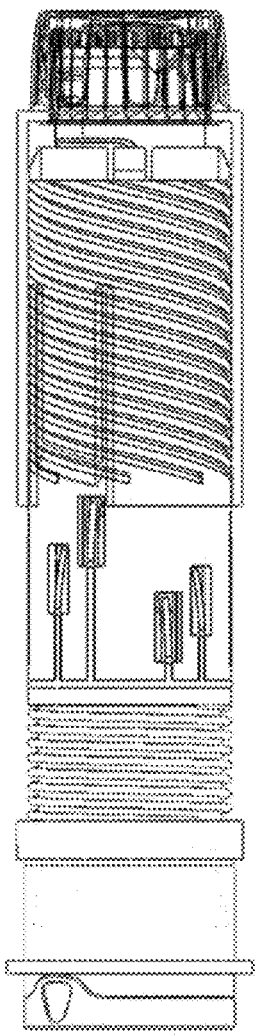
FIG. 33a is a side view of the device according to the sixth embodiment of the invention.
Figure 33B:
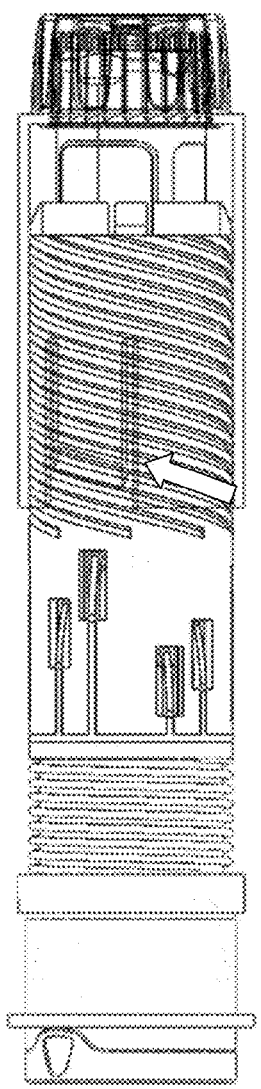
FIG. 33b is the same as FIG. 33a but with more dose having been dialed.
Figure 33C:
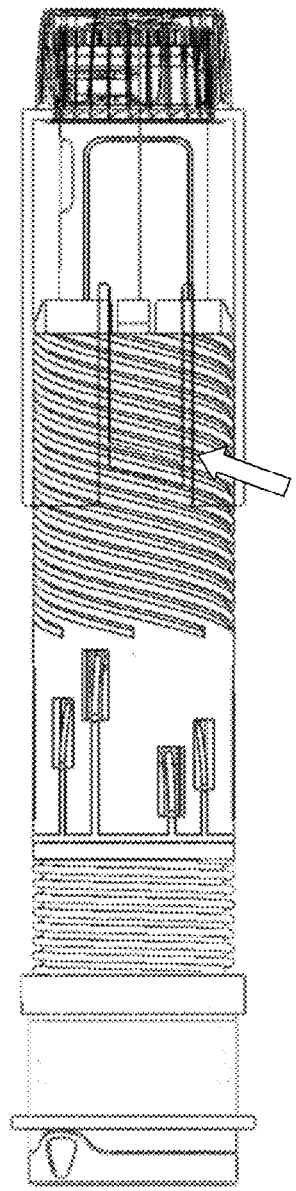
FIG. 33c is the same as FIGS. 33a and 33b but with even more dose having been dialed into the device.
Figures 34A, 34B, 34C:
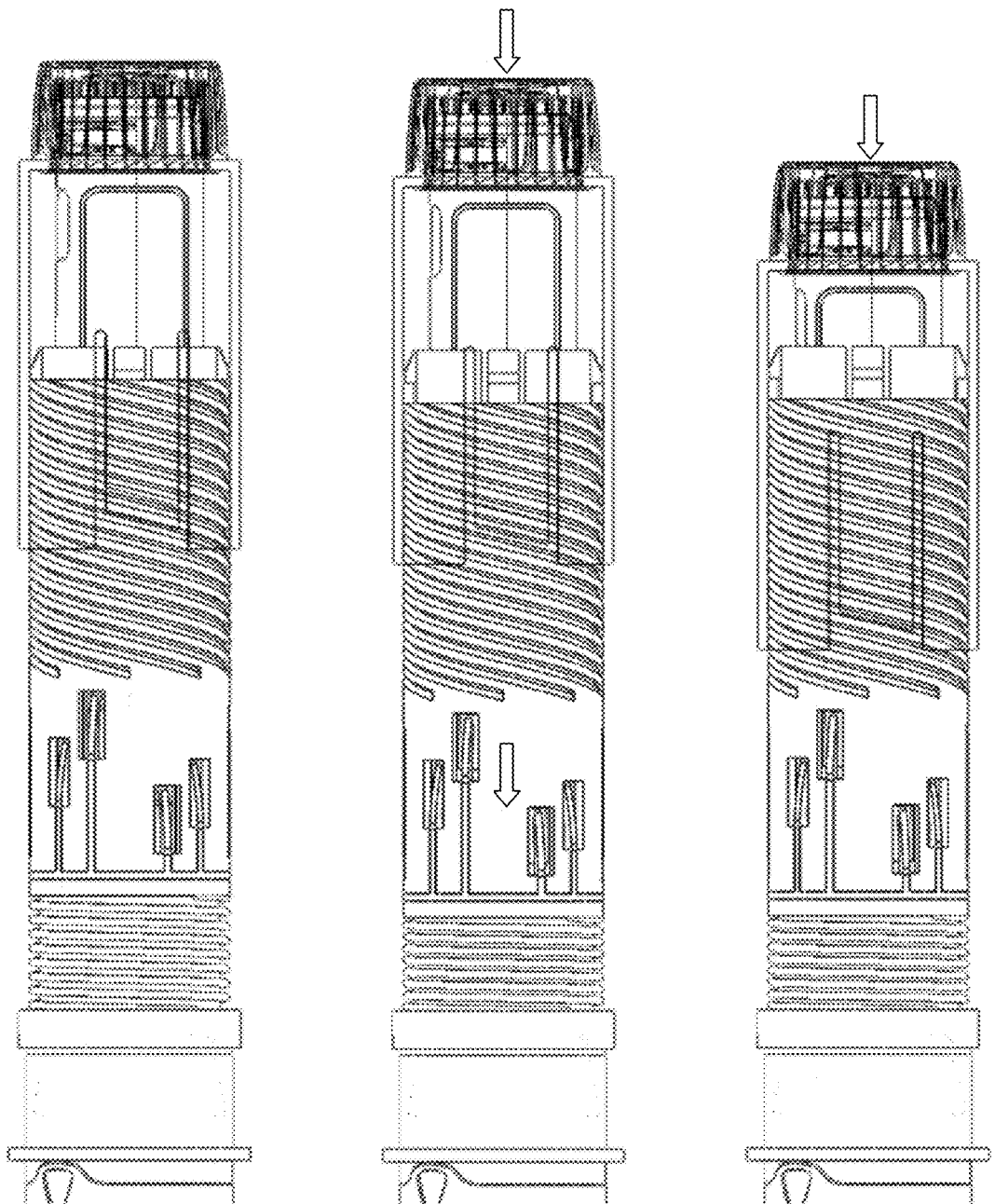
FIG. 34a, FIG. 34b and FIG. 34c show the device according to the sixth embodiment of the invention as a dose is delivered.

When the user wishes to dispense a dose, they press downwards on the rotatable dial 108. As such, the rotatable dial 108 is displaced towards the cartridge, which is downwards in the Figure. As the thread features on the rotatable dial contact the ramp's lower thread surface on the sensor sleeve 380, the sensor sleeve is displaced axially. Axial displacement occurs until the sensor sleeve reaches an end stop, which is best shown in FIG. 33. During this movement, the contacts 212 are forced up ramps 326 on the outer body 102 such that they are no longer aligned with the windows 324 in the outer body, and thus are no longer in contact with the helical tract 300 on the number sleeve. The rotatable dial 108 continues to move axially during the dispense operation.

In all of the above-described embodiments, the processor 202 is capable of determining the extent of rotation of the rotatable sleeve 406 (and thus how far it has traveled axially) by analysing which contacts 212a-212g engage conductive segments 302 and which contacts engage non-conductive segments 304.

In all of the above-described embodiments, the helical track 300 may be formed by wrapping a metallic strip around the encoder sleeve 406, or other component on which the helical track 300 is provided as the case may be. Such a metallic strip may have a non-conductive backing to support the metallic layer. The non-conductive backing may have an adhesive on the reverse side for securing the strip to the rotatable sleeve 406 etc. The helical track 300 may alternatively comprise conductive ink printed onto a non-conductive substrate. This non-conductive substrate may be the encoder sleeve 406, or other component on which the helical track 300 is provided as the case may be.

In all of the embodiments, having determined the drug dose which has been dispensed, the processor 202 may store the result in the flash memory 205. The display 210 may be controlled to display the result of the dispensed dose determination. The display 210 may display the result of the dispensed dose determination for a predetermined time, for example 60 seconds. Alternatively or in addition, the dispensed dose history may be retrieved electronically from the flash memory 205by a user of the device 100 or by a health care professional. During dialing of the device, the dialed dose may be indicated to the user in any conventional way, for example by use of numerals printed on the encoded member. In some other embodiments, the dialed dose is not determined or indicated to the user.

Sensing of the presence or absence of track is performed using a contact and the processor. At a general level, this may involve hardware that compares a voltage signal provided by the contact with a threshold and indicting the presence or absence of track through an output that indicates whether the voltage exceeded or did not exceed respectively the threshold. In a processor implementation, it may involve buffering the signal provided by the contact, for instance using an inverter gate or other buffer, sampling the buffered signal and comparing the sampled signal to a reference. Other ways of sensing the presence or absence of track will be apparent to the skilled person.

Finally, it will be appreciated that the above-described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalisation thereof and during the prosecution of the present application or of any application derived therefrom, new claims may be formulated to cover any such features and/or combination of such features.

The invention claimed is:

1. A drug delivery device, comprising: a housing having a longitudinal axis; an axially moveable component that is moveable along the longitudinal axis between a dose dialing position and a dose delivery position when a user operates the device to deliver a dose of drug; an encoder sleeve;

an encoder pattern provided on the encoder sleeve, the encoder pattern comprising relatively conductive portions and relatively non-conductive portions that together comprise coded information; a contact-supporting component; and plural electrical contacts provided on the contact-supporting component, wherein the plural electrical contacts contact the encoder pattern when a dose delivery button is in the dose dialing position and wherein the device is configured to move the contact supporting component relative to the encoder sleeve as the axially moveable component moves from the dose dialling position to the dose delivery position such as to move the electrical contacts into positions where they do not contact the encoder pattern.

2. A drug delivery device as claimed in claim 1, wherein the axially moveable component is a grip sleeve that is external to the housing, is rotationally fixed relative to the housing and is axially moveable relative to the housing.

3. A drug delivery device as claimed in claim 1, wherein the contacts are provided on a contact sleeve and extend through windows in an intermediate sleeve to contact the encoder pattern when the device is in the dose dialling position and do not extend through the windows in the intermediate sleeve to contact the encoder patter when the device is in the dose delivery position.

4. A drug delivery device as claimed in claim 3, wherein the device is configured to move the intermediate sleeve relative to the contact sleeve as the device moves from the dose dialling position to the device is in the dose delivery position.

5. A drug delivery device as claimed in claim 3, wherein the device is configured to rotate the intermediate sleeve relative to the contact sleeve as the device moves from the dose dialling position to the dose delivery position.

6. A drug delivery device as claimed in claim 4, wherein the device is configured to move the intermediate sleeve axially relative to the contact sleeve as the device moves from the dose dialling position to the dose delivery position.

7. A drug delivery device as claimed in claim 1, wherein the device is configured to move the contact-supporting component relative to the encoder sleeve as the axially moveable component moves from the dose dialling position to the dose delivery position such as to move the electrical contacts into positions where they do not contact the encoder pattern as the device moves from the dose dialling position to the dose delivery position.

8. A drug delivery device as claimed in claim 1, wherein the encoder sleeve is a button sleeve that is axially constrained with the dose delivery button and that is configured to travel on two different axially separated helixes in dialling and dispensing modes respectively.

9. A drug delivery device as claimed in claim 8, configured such that the plural electrical contacts move from the encoder pattern down a ramp surface as the mode of the drug delivery device changes from dialling mode to dose delivery mode.

10. A drug delivery device as claimed in claim 9, wherein as the device is moved from the dialling mode to the delivery mode, the plural electrical contacts slide down the ramp surface into a recess.

11. A drug delivery device as claimed in claim 9, wherein a spring is configured to be compressed as the device is moved from the dialling mode to the delivery mode and to cause the plural electrical contacts to slide up the ramp surface after pressure is released from the dose delivery button.

12. A drug delivery device as claimed in claim 1, comprising an intermediate sleeve rotationally fixed relative to the housing and including thread features that engage with thread features of a button sleeve that is axially constrained with the dose delivery button.

13. A drug delivery device as claimed in claim 12, wherein the contact supporting component comprises a split contact sleeve provided with ramp surfaces, the device comprising a ramp feature on the intermediate sleeve that contact the ramp surfaces of the contact sleeve.

14. A drug delivery device as claimed in claim 13, wherein a spring is configured to be compressed when a user presses the dose delivery button to move the button sleeve and the intermediate sleeve such that the ramp surfaces act against the ramp feature to force first and second portions of the contact sleeves apart.

\* \* \* \* \*